(12) United States Patent
Murakami et al.

(10) Patent No.: US 11,733,232 B2
(45) Date of Patent: Aug. 22, 2023

(54) METHOD FOR PRODUCING DISEASE MODELING NON-HUMAN ANIMAL, DISEASE MODELING NON-HUMAN ANIMAL, AND METHOD FOR SCREENING DRUG AND METHOD FOR DETERMINING RISK OF DISEASE USING THE SAME

(71) Applicant: National University Corporation Hokkaido University, Sapporo (JP)

(72) Inventors: Masaaki Murakami, Sapporo (JP); Daisuke Kamimura, Sapporo (JP); Yasunobu Arima, Sapporo (JP)

(73) Assignee: National University Corporation Hokkaido University, Sapporo (JP)

( * ) Notice: Subject to any disclaimer, the term of this patent is extended or adjusted under 35 U.S.C. 154(b) by 969 days.

(21) Appl. No.: 16/490,145

(22) PCT Filed: Mar. 1, 2018

(86) PCT No.: PCT/JP2018/007901
§ 371 (c)(1),
(2) Date: Aug. 30, 2019

(87) PCT Pub. No.: WO2018/159787
PCT Pub. Date: Sep. 7, 2018

(65) Prior Publication Data
US 2020/0049696 A1 Feb. 13, 2020

(30) Foreign Application Priority Data
Mar. 1, 2017 (JP) ................... 2017-038115

(51) Int. Cl.
*G01N 33/50* (2006.01)
*A01K 67/027* (2006.01)

(52) U.S. Cl.
CPC ....... *G01N 33/5008* (2013.01); *A01K 67/027* (2013.01); *A01K 2267/0318* (2013.01); *A01K 2267/0356* (2013.01); *A01K 2267/0368* (2013.01); *A01K 2267/0375* (2013.01)

(58) Field of Classification Search
CPC .............. G01N 33/5008; A01K 67/027; A01K 2267/0356; A01K 2267/0368
USPC ........................................................ 800/18
See application file for complete search history.

(56) References Cited

U.S. PATENT DOCUMENTS

| 2004/0121004 A1 | 6/2004 | Taneja |
| 2007/0203216 A1 | 8/2007 | Ebert et al. |
| 2010/0221219 A1 | 9/2010 | Foussat |
| 2010/0303866 A1 | 12/2010 | Saint-Remy |
| 2011/0003822 A1 | 1/2011 | Burgey |
| 2011/0059107 A1 | 3/2011 | Allison et al. |
| 2015/0132264 A1 | 5/2015 | Kelly et al. |
| 2015/0218256 A1 | 8/2015 | Perron et al. |
| 2018/0051087 A1 | 2/2018 | Ravetch et al. |
| 2020/0049696 A1 | 2/2020 | Murakami et al. |
| 2020/0188491 A1 | 6/2020 | Toda et al. |

FOREIGN PATENT DOCUMENTS

| CN | 106544430 A | 3/2017 |
| JP | 2001519154 A | 10/2001 |
| JP | 2008523838 A | 7/2008 |
| JP | 2009526786 A | 7/2009 |
| JP | 2011502149 A | 1/2011 |
| JP | 2012107021 A | 6/2012 |
| JP | 2013503192 A | 1/2013 |
| JP | 2014071016 A | 4/2014 |
| JP | 2014534957 A | 12/2014 |
| JP | 2015142578 A | 8/2015 |
| JP | 2016500651 A | 1/2016 |
| WO | 2006067124 A2 | 6/2006 |

(Continued)

OTHER PUBLICATIONS

Arima, 2015, Mediators of Inflammation, vol. 2013, pp. 1-8, Article ID 898165.*
Kamimura (2018, International Immunology, 30:281-289).*
Arima et al., Ceil, 148:447-57 (2012).
Arima et al., eLife, 4:e08733, pp. 1-23 (2015).
Arima et al., eLife, 6:e25517, pp. 1-27 (2017).
Benamar et al., European Journal of Pharmacology, 592:93-95 (2008).
Caso et al., Current Molecular Medicine, 8:299-312 (2008).
International Search Report and Written Opinion for International Application No. PCT/JP2018/007901, dated Jun. 5, 2018, 13 pages.
Kim et al., Mol. Brain, 4(6):1-10 (2011).

(Continued)

*Primary Examiner* — Valarie E Bertoglio
(74) *Attorney, Agent, or Firm* — RatnerPrestia

(57) ABSTRACT

[Problem] The objectives of the present invention are to provide a method for making an animal that has been stressed, in particular, chronically stressed, affect or develop a specific disease or symptom, and, through elucidating the process from loading stress to affection or onset of the disease or symptom, to provide a useful tool for research and development of preventing or treating methods of the disease or symptom. [Solution] The present invention relates to a method for producing a disease modeling non-human animal having cerebrovascular inflammation, the disease modeling non-human animal, a method for screening a drug using the disease modeling non-human animal, a method for determining the risk of a disease using the presence of cerebrovascular inflammation as an indicator, and a pharmaceutical for preventing and/or treating progressive multiple sclerosis or the like. The present invention enables developing pharmaceuticals for the above described diseases or the like and performing researches for elucidating their pathogenic mechanisms. The present invention also enables determining the risk of affection or onset of progressive multiple sclerosis or the like and preventing and/or treating progressive multiple sclerosis or the like.

14 Claims, 25 Drawing Sheets
Specification includes a Sequence Listing.

(56) References Cited

FOREIGN PATENT DOCUMENTS

| WO | 2008058018 A2 | 5/2008 |
| WO | 2015057939 A1 | 4/2015 |
| WO | 2016131944 A1 | 8/2016 |
| WO | 2016141262 A1 | 9/2016 |
| WO | 2018034334 A1 | 2/2018 |
| WO | 2018159787 A1 | 9/2018 |

OTHER PUBLICATIONS

Miller et al., Curr. Protoc. Immunol., Unit 15.1, pp. 1-25 (2007).
Miyazaki et al., PLOS One, 8(1):e55452, pp. 1-10 (2013).
Ogura et al., Immunity, 29:628-36 (2008).
Ueda et al., International Immunology, 18(9):1397-1404 (2006).
Japanese Notice of Reasons for Refusal for Japanese Application No. 2019-503129, dated Jan. 25, 2022, with translation, 9 pages.
Dong et al, "Secretion Protein VSTM2A Is A Novel Tumor Suppressor and Associates with Colorectal Cancer Patient Survival" United European Gastroenterol. J., 4(5):A280-281 (2016).
Rossini et al., "VSTM2L is A Novel Secreted Antagonist Of The Neuroprotective Peptide Humanin", FASEB Journal, 25(2):1983-2000 (2011).
Secco et al., "Amplification of Adipogenic Commitment by VSTM2A", Cell Reports., 18:93-106 (2017).
International Search Report and Written Opinion for International Application No. PCT/JP2019/034497, dated Dec. 3, 2019, 15 pages.
International Preliminary Report on Patentability for International Application No. PCT/JP2019/034497, dated May 25, 2020, 14 pages.
Partial Supplementary Search Report for EP Application No. 19855524.5, dated May 24, 2022, 21 pages.
Ciotti et al., "Disease-Modifying Treatment in Progressive Multiple Sclerosis", Current Treatment Options In Neurology, 20(12), 26 pages (2018).
Marques et al., "Targeting CCL5 in Inflammation", Expert Opinion on Therapeutic Targets, 17(12), 23 pages, (2013).
Schwarzmaier et al., "Peripheral Monocyte Functions and Activation in Patients with Quiescent Crohn's Disease", PLOS ONE, 8(4), 7 pages (2013).
Extended European Search Report for European Application No. 19 855 524.5, dated Aug. 30, 2022, 19 pages.

* cited by examiner

A

B

A

B

METHOD FOR PRODUCING DISEASE MODELING NON-HUMAN ANIMAL, DISEASE MODELING NON-HUMAN ANIMAL, AND METHOD FOR SCREENING DRUG AND METHOD FOR DETERMINING RISK OF DISEASE USING THE SAME

CROSS-REFERENCE TO RELATED APPLICATIONS

This application is a U.S. national phase application of International Application No. PCT/JP2018/007901, filed Mar. 1, 2018 claiming the benefit of Japanese Application No. 2017-038115, filed Mar. 1, 2017, the contents of each of which are incorporated herein by their entireties for all purposes.

The Sequence Listing for this application is labeled "P16HU05WO_ST25.txt" which was created on Aug. 29, 2019 and is 1.49 KB. The entire content of the sequence listing is incorporated herein by reference in its entirety.

TECHNICAL FIELD

The present invention relates to a method for producing a disease modeling non-human animal having cerebrovascular inflammation, the disease modeling non-human animal, a method for screening a drug using the disease modeling non-human animal, a method for determining the risk of a disease using the presence of cerebrovascular inflammation as an indicator, and a pharmaceutical containing a substance including a γ-aminobutyric acid (GABA) receptor agonist as an active ingredient for preventing and/or treating progressive multiple sclerosis, gastroenteritis, myocardial disorder, or sudden death.

BACKGROUND ART

Various external factors such as noise, frigidity, drugs, bacterial infections, as well as human relations and work accountability and the like, are generally referred to as stress, and stress is empirically known to cause non-specific abnormal conditions to human body. For example, stress can damage mental and physical homeostasis maintenance functions, and bring relatively mild diseases or symptoms such as asthma, spot baldness, urinary frequency, tinnitus, dizziness, and the like.

Stress can furthermore induce neurotic diseases such as depression, panic disorder, and anxiety disorder, gastrointestinal ulceration, irritable bowel syndrome, serious diseases or symptoms such as ischemic cardiac diseases, and sometimes stress can induce directly life-threatening symptoms, for example, sudden death. Sudden death is defined as natural death which occurs within 24 hours from the onset, and its typical example is cardiac sudden death caused by cardiac diseases.

In order to investigate effective preventing methods or treating methods for various diseases caused by stress, medical researches on associations among stress and various diseases or symptoms are in progress. For example, through a research using a model animal, it is reported that brain-gut interaction is involved with interactions among nerve-constituting elements, for example, the autonomic nerve system, the central nerve system, stress system such as hypothalamic-pituitary-adrenal axis, and corticotropin-releasing factor system, and gut factor such as intestinal barrier, luminal microbiota, and intestinal immune response (Non-patent literature 1).

Moreover, through molecular-biological researches on association of stress with various diseases or symptoms, it becomes elucidated that stress hormones represented by corticotropin-releasing hormone (CRH), neurotransmitters such as noradrenaline, serotonin and dopamine, and other various neuropeptides are involved with biological responses to stress.

The present inventors, by using an animal model of multiple sclerosis (experimental autoimmune encephalomyelitis, EAE model), investigated the process from loading stress of "pain" to onset of symptoms of multiple sclerosis, and found that symptoms of multiple sclerosis develops through steps of the activation of sensory nerves by pain, activation of sympathetic nerves, infiltration of immune cells into ventral vessels in the fifth lumbar cord, and activation of inflammation amplifier by the infiltration (gateway reflex; Non Patent Literature 2). This study results advocate that inhibiting neural network originating from pain, for example, by administrating an analgesic agent, can provide new means for not only removing pain but also preventing relapse of multiple sclerosis.

Thus, elucidating the process from loading stress to affection or onset of a specific disease or symptom may lead to proposing a new approach, finding a new drug target, and the like, for preventing or treating the disease or symptom.

CITATION LIST

Non-Patent Literatures

Non-Patent Literature 1: Caso, J. R. et al., Current molecular medicine, 2008, Vol. 8, pp. 299-312
Non-Patent Literature 2: Arima, Y. et al., eLife, 2015, 4, 08733.

SUMMARY OF INVENTION

Technical Problem

The objectives of the present invention are to provide a method for making an animal that has been stressed, in particular, chronically stressed, affect or develop a specific disease or symptom, and, through elucidating the process from loading stress to affection or onset of the disease or symptom, to provide a useful tool for research and development of preventing or treating methods of the disease or symptom.

Solution to the Problem

The present inventors found that, when CD4 positive T cells reactive to an antigen derived from the central nervous tissue are made to exist in the body of a non-human animal being under stress condition, inflammation occurs at cerebral blood vessels of the animal and the animal exhibits various diseases or symptoms such as progressive multiple sclerosis, gastroenteritis, myocardial disorder, or sudden death, and the present inventors completed the following invention.

(1) A method for producing a disease modeling non-human animal having inflammation at a cerebral blood vessel thereof, including a step of making CD4 positive T cells exist in the body of a non-human animal being under stress condition, wherein the CD4 positive T cells are reactive to an antigen derived from the central nervous tissue.

(2) The method according to (1), wherein the cerebral blood vessel is a blood vessel in the boundary area of the third ventricle, thalamus, and dentate gyrus.
(3) The method according to any one of (1) to (2), wherein the disease modeling non-human animal is an animal having at least one disease or symptom selected from the group consisting of progressive multiple sclerosis, gastroenteritis, myocardial disorder, and sudden death.
(4) The method according to any one of (1) to (3), wherein the step of making CD4 positive T cells exist in the body of a non-human animal being under stress condition is a step of transferring CD4 positive T cells into a non-human animal on which stress has been loaded.
(5) A disease modeling non-human animal having inflammation at a blood vessel in the boundary area of the third ventricle, thalamus, and dentate gyrus thereof, and having at least one disease or symptom selected from the group consisting of progressive multiple sclerosis, gastroenteritis, myocardial disorder, and sudden death.
(6) A method for screening a drug for preventing and/or treating at least one disease or symptom selected from the group consisting of progressive multiple sclerosis, gastroenteritis, myocardial disorder, and sudden death, including:
  (i) a step of making CD4 positive T cells exist in the body of a non-human animal being under stress condition, wherein the CD4 positive T cells are reactive to an antigen derived from the central nervous tissue, (ii) a step of administering a test substance to the non-human animal at any time point before starting the step (i) through after completing the step (i), and
  (iii) a step of observing development, progression, or occurrence of at least one disease or symptom selected from the group consisting of cerebrovascular inflammation, progressive multiple sclerosis, gastroenteritis, myocardial disorder, and sudden death, in the non-human animal to which the test substance is administered, and comparing the observation results with those in a non-human animal to which the test substance is not administered.
(7) A method for determining the risk of a subject of being affected with or developing at least one disease or symptom selected from the group consisting of progressive multiple sclerosis, gastroenteritis, myocardial disorder, and sudden death, including,
  (a) a step of detecting the presence of inflammation at a blood vessel in the boundary area of the third ventricle, thalamus, and dentate gyrus in the subject, and
  (b) a step of determining that the subject has a high risk of being affected with or developing at least one disease or symptom selected from the group consisting of progressive multiple sclerosis, gastroenteritis, myocardial disorder, and sudden death when inflammation is detected in the step (a).
(8) A pharmaceutical containing an antibody to CC chemokine ligand 5 (CCL5) as an active ingredient for preventing and/or treating at least one disease or symptom selected from the group consisting of progressive multiple sclerosis, gastroenteritis, myocardial disorder, and sudden death.
(9) A pharmaceutical containing a γ-aminobutyric acid (GABA) receptor agonist as an active ingredient for preventing and/or treating at least one disease or symptom selected from the group consisting of progressive multiple sclerosis, gastroenteritis, myocardial disorder, and sudden death.
(10) A pharmaceutical containing an ATP receptor antagonist as an active ingredient for preventing and/or treating at least one disease or symptom selected from the group consisting of progressive multiple sclerosis, gastroenteritis, myocardial disorder, and sudden death.
(11) A pharmaceutical containing a proton pump inhibitor as an active ingredient for preventing and/or treating at least one disease or symptom selected from the group consisting of progressive multiple sclerosis, myocardial disorder, and sudden death.
(12) A pharmaceutical containing an antibody to lymphocyte antigen 6 family member G5C (LY6G6C) as an active ingredient for preventing and/or treating at least one disease or symptom selected from the group consisting of progressive multiple sclerosis, gastroenteritis, myocardial disorder, and sudden death.
(13) A pharmaceutical containing an antibody to α2C adrenergic receptor as an active ingredient for preventing and/or treating at least one disease or symptom selected from the group consisting of progressive multiple sclerosis, gastroenteritis, myocardial disorder, and sudden death.
(14) The pharmaceutical according to any one of (8) to (13), wherein the disease or symptom is a disease or symptom caused by stress load.

Advantageous Effects of the Invention

Non-human animals produced by the method for producing a disease modeling animal according to the present invention reflect pathological conditions of progressive multiple sclerosis, gastroenteritis, myocardial disorder, or sudden death, and the animals are useful in developing pharmaceuticals for preventing or treating these diseases or symptoms, and are useful in researches for elucidating their pathogenic mechanisms. Moreover, according to the present invention, the risk of affection or onset of progressive multiple sclerosis, gastroenteritis, myocardial disorder, or sudden death can be determined, and this enables preventive treatment before affection or onset to subjects with a high risk of affection or onset of these diseases or symptoms. Furthermore, by using the pharmaceutical according to the present invention, at least one disease or symptom selected from the group consisting of progressive multiple sclerosis, gastroenteritis, myocardial disorder, and sudden death can be prevented and/or treated.

BRIEF DESCRIPTION OF THE DRAWINGS

FIG. 1A shows changes of EAE clinical scores over time, and FIG. 1B shows the mortality 10 days after EAE-pathogenic CD4 positive T cell transfer.

FIG. 2A shows changes of EAE clinical scores over time, and FIG. 2B shows the mortality 10 days after EAE-pathogenic CD4 positive T cell transfer.

FIG. 4A shows fecal occult blood scores, and FIG. 4B shows hematocrits.

FIG. 5A shows bloody content scores in various digestive tract parts, FIG. 5B shows gastric photos, and FIG. 5C shows hematoxylin-eosin staining images of stomach tissue, duodenum tissue, jejunum tissue, and ileum tissue.

FIG. 6A shows changes of EAE clinical scores over time, and FIG. 6B shows the mortality 10 days after EAE-pathogenic CD4 positive T cell transfer, and FIG. 6C shows fecal occult blood scores.

FIG. 9A shows photographs of the upper heart parts (regions including the atrium, blood vessels, and cardiac valves), and FIG. 9B shows photographs of lower heart parts (the ventricle).

FIG. 16A shows changes of EAE clinical scores over time, and FIG. 16B shows the mortality 10 days after EAE-pathogenic CD4 positive T cell transfer.

FIG. 19A shows changes of EAE clinical scores over time, and FIG. 19B shows the mortality 10 days after EAE-pathogenic CD4 positive T cell transfer.

FIG. 20A shows the mortality 2 days after microinjection, and FIG. 20B shows fecal occult blood scores.

FIG. 23A shows changes of EAE clinical scores over time, and FIG. 23B shows the mortality 10 days after EAE-pathogenic CD4 positive T cell transfer.

FIG. 29A shows changes of EAE clinical scores over time, and FIG. 29B shows the mortality 10 days after EAE-pathogenic CD4 positive T cell transfer, and FIG. 29C shows fecal occult blood scores.

FIG. 32A shows changes of EAE clinical scores over time, and FIG. 32B shows the mortality 10 days after EAE-pathogenic CD4 positive T cell transfer, and FIG. 32C shows fecal occult blood scores.

FIG. 35A shows the mortality 10 days after EAE-pathogenic CD4 positive T cell transfer, and FIG. 35B shows fecal occult blood scores.

FIG. 37A shows changes of EAE clinical scores over time, and FIG. 37B shows the mortality 10 days after EAE-pathogenic CD4 positive T cell transfer, and FIG. 37C shows fecal occult blood scores.

FIG. 39A shows changes over time of EAE clinical scores of mice to which an anti-LY6G6C antibody was administered, and FIG. 39B shows changes over time of EAE clinical scores of mice to which an anti-α2C adrenergic receptor antibody was administered.

DESCRIPTION OF THE EMBODIMENTS

Figure 1:
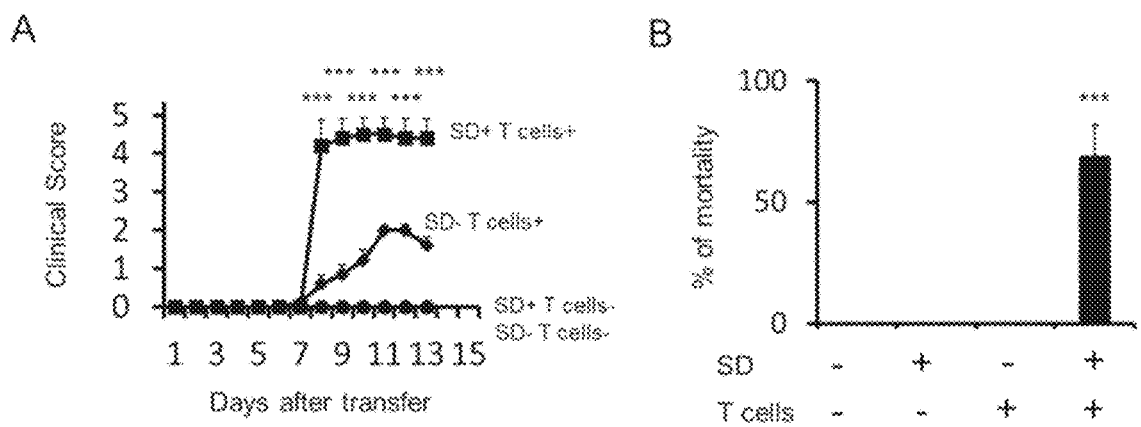
FIG. 1 illustrates graphs indicating pathological conditions of mice in which sleep disorder was induced followed by transfer of experimental autoimmune encephalomyelitis (EAE)-pathogenic CD4 positive T cells (SD+ T cells+), mice into which EAE-pathogenic CD4 positive T cells were transferred without induction of sleep disorder (SD− T cells+), mice which underwent sleep disorder induction alone (SD+ T cells−), and mice with neither treatment (SD− T cells−) in Example 1 (1).

Method for Producing a Disease Modeling Animal and the Disease Modeling Animal

The first aspect of the present invention relates to a method for producing a disease modeling non-human animal having cerebrovascular inflammation at a cerebral blood vessel thereof, including a step of making CD4 positive T cells exist in body of a non-human animal being under stress condition, wherein the CD4 positive T cells are reactive to an antigen derived from the central nervous tissue.

A medical term "stress" refers to both of an adverse factor (the cause of stress, stressor) added from outside of the body and the defense reaction resulted therefrom (Nanzando's Medical Dictionary, 19$^{th}$ Edition). Herein, the former adverse factor is referred to as stress, being exposed to an adverse factor is referred to as being stressed or being loaded with stress, and the latter defense reaction is referred to as stress reaction. According to so-called stress theory, stress reaction is a series of reactions called adaptation syndrome which occurs in the living body to defense itself from stress. Stress reaction can be divided into three stages: the alarm reaction stage from stress load to developing adaptation reaction to stress, the resistance stage during which resistance to stress is exerted by the adaptation reaction, and the exhaustion stage during which, due to prolonged stress load, the resistance becomes lost. Herein, being at any stage of the stress reaction may be referred to as being under stress condition.

The non-human animal used in the present invention is not limited, so long as it can be used as a non-human laboratory animal. The non-human animal is preferably a non-human animal which is known to develop experimental autoimmune encephalomyelitis (EAE) by administration of an antigen derived from the central nervous tissue or administration of CD4 positive T cells reactive to the antigen. Examples of the non-human animal model include mice, rats, guinea pigs, rabbits, chickens, and primates.

The non-human animal under stress condition used in the present invention can be produced by stress load to a non-human animal. Such stress is not limited so long as it can make a non-human animal under stress condition, that is, it can induce stress reaction in the non-human animal, and chronic stress in which stress reaction is sustained over long periods is suitably utilized. Examples of chronic stress include perpetual avoidance from water on a wheel (PAWW) stress that causes sleep disorder (Miyazaki, K. et al., PloS one, 2013, 8, e55452), wet bedding, social defeat stress, and maternal separation stress.

Stress condition in a non-human animal can be confirmed by detecting presence of stress reaction, for example, by measuring blood level of corticosteroid, such as cortisol, aldosterone, and androgen, whose secretion is known to be enhanced responding to stress. As shown in the following Examples, the present inventors revealed that stress enhances expression of CCL5 at perivascular tissue in the boundary area of the third ventricle, thalamus, and dentate gyrus, and that stress triggers sympathetic activation in the paraventricular nucleus (PVN). Accordingly, increased expression level of CCL5 at the perivascular tissue described above and enhanced phosphorylation of cfos and CREB associated with sympathetic activation in the PVN can be utilized as indicators of being under stress condition.

The antigen derived from the central nervous tissue is an antigen which is used in induction of EAE. EAE is an autoimmune disease model emulating pathological conditions of multiple sclerosis. The antigen derived from the central nervous tissue utilized in the present invention may be any antigen having an EAE-inducing ability, and a homogenate of the central nervous tissue may be used as it is, wherein the homogenate is prepared from another animal individual of the same species as or different species from that of the animal individual to which the antigen is to be administered. However, preferably, proteins contained in myelin sheath (myelin), especially intact proteins or partial peptides of proteolipid protein (PLP), myelin oligodendrocyte glycoprotein (MOG), or myelin basic protein (MBP) are used. Examples of such proteins or their partial peptides are described in known literatures related to EAE, for example, Miller, S. et al., Curr. Protoc. Immunol., 2010, Unit 15.1, which is incorporated herein by reference.

The CD4 positive T cells which are reactive to an antigen derived from the central nervous tissue in the present invention are CD4 positive T cells capable of eliciting immune reaction in response to the antigen derived from the central nervous tissue. These cells are known to be induced on administration of an antigen derived from the central nervous tissue into the living body thereby inducing EAE, and are also referred to as EAE-pathogenic CD4 positive T cells. Means for making the CD4 positive T cells exist in the body of an animal are known. One of the means is a method in which endogenous CD4 positive T cells reactive to the antigen are generated by administering the antigen derived from the central nervous tissue to the animal, and another one of the means is a method in which CD4 positive T cells reactive to the antigen are collected from an animal to which the antigen derived from the central nervous tissue was administered and the collected CD4 positive T cells reactive to the antigen are transferred into another non-human animal. EAE induced by the former method is referred to as an active EAE model, and EAE induced by the latter method is referred to as a passive EAE model.

In the method for producing a disease modeling animal according to the present invention, the step of making the CD4 positive T cells exist in the body of a non-human animal being under stress condition can be achieved by generating endogenous CD4 positive T cells reactive to the antigen through administering the antigen derived from the central nervous tissue to the non-human animal under stress condition, or by collecting CD4 positive T cells reactive to the antigen from an animal to which the antigen derived from the central nervous tissue was administered and transferring the CD4 positive T cells reactive to the antigen into another non-human animal under stress condition, in accordance with the method for inducing the active EAE model or the passive EAE model described above.

This step can be performed by appropriately setting detailed conditions, such as conditions of the dosage and administration period of the antigen derived from the central nervous tissue, and preparation of the CD4 positive T cells reactive to the antigen derived from the central nervous tissue, with reference to known methods used in induction of the active EAE model or the passive EAE model, for example, the method described in Miller, S. et al., Curr. Protoc. Immunol., 2010, Unit 15.1. The antigen derived from the central nervous tissue can be used in combination with adjuvants such as complete Freund's adjuvant and incomplete Freund's adjuvant and/or with pertussis toxin, and thus production efficiency of disease modeling animals can be improved.

Sequential orders of administering the antigen derived from the central nervous tissue or CD4 positive T cells reactive to the antigen and loading stress to the non-human animal are not limited, so long as the animal is under stress condition when CD4 positive T cells reactive to the antigen derived from the central nervous tissue are made to exist in the body of the animal. CD4 positive T cells reactive to the antigen may be made to exist in the body of the animal through loading stress on the animal followed by administering the antigen derived from the central nervous tissue or CD4 positive T cells reactive to the antigen. Conversely, CD4 positive T cells reactive to the antigen may also be made to exist in the body of the animal through administering the antigen derived from the central nervous tissue or CD4 positive T cells reactive to the antigen to make CD4 positive T cells reactive to the antigen exist in the body of the animal followed by loading stress while these cells exist effectively in the body of the animal.

In the method for producing a disease modeling animal according to the present invention, the step of making CD4 positive T cells exist in body of a non-human animal being under stress condition is preferably a step of transferring CD4 positive T cells into a non-human animal on which stress has been loaded, wherein the CD4 positive T cells are reactive to an antigen derived from the central nervous tissue.

The method for producing a disease modeling animal in the first aspect described above can provide a disease modeling non-human animal having inflammation at a cerebral blood vessel thereof, especially at a blood vessel in the boundary area of the third ventricle, thalamus, and dentate gyrus. While EAE is a disease in which the central nervous tissue is attacked by autoimmune system to cause inflammation at various parts of the brain and spinal cord, the present inventors revealed that, the above described disease modeling animal develops various diseases and symptoms such as progressive multiple sclerosis, gastroenteritis, myocardial disorder, or sudden death by inflammation occurring at a specific blood vessel in the boundary area of the third ventricle, thalamus, and dentate gyrus. Another aspect of the present invention relates to such a disease modeling animal, that is, a disease modeling non-human animal having inflammation at a blood vessel in the boundary area of the third ventricle, thalamus, and dentate gyrus, and having at least one disease or symptom selected from the group consisting of progressive multiple sclerosis, gastroenteritis, myocardial disorder, and sudden death.

Multiple sclerosis (MS) can be divided into four subgroups: relapsing-remitting MS, secondary progressive MS (the late phase of relapsing-remitting type), primary progressive MS, and progressive-relapsing MS. The disease modeling non-human animal described above exhibits continuous exacerbation of EAE pathological conditions, which reflect pathological conditions of progressive multiple sclerosis found in subgroups of MS other than relapsing-remitting MS. In addition, the disease modeling non-human animal described above exhibits pathological conditions of sudden death, which causes to death within few days from when no EAE pathological condition is exhibited, pathological conditions of gastroenteritis including bleeding and inflammation in the stomach and upper small bowel, and pathological conditions of myocardial disorder including myocardial cell death or heart failure.

Method for Screening

Further aspect of the present invention relates to a method for screening a drug for preventing and/or treating at least one disease or symptom selected from the group consisting of progressive multiple sclerosis, gastroenteritis, myocardial disorder, and sudden death, including, (i) a step of making CD4 positive T cells exist in the body of a non-human animal being under stress condition, wherein the CD4 positive T cells are reactive to an antigen derived from the central nervous tissue, (ii) a step of administering a test substance to the non-human animal at any time point before starting the step (i) through after completing the step (i), and (iii) a step of observing development, progression, or occurrence of at least one disease or symptom selected from the group consisting of cerebrovascular inflammation, progressive multiple sclerosis, gastroenteritis, myocardial disorder, and sudden death, in the non-human animal to which the test substance is administered, and comparing the observation results with those in a non-human animal to which the test substance is not administered.

The step (i) is a step of making CD4 positive T cells exist in the body of a non-human animal being under stress condition, wherein the CD4 positive T cells are reactive to an antigen derived from the central nervous tissue. This step can be performed in the same way as in the first aspect of the method for producing a disease modeling animal.

The step (ii) is a step in which a test substance is administered to the non-human animal at any time point before starting the step (i) through after completing the step (i). The timing of administering the test substance can be determined based on what kind of effects of drugs to be obtained by the screening are expected. Specifically, if a drug having a preventing effect or a preventing and treating effect is desired, administration of the test substance is performed before induction of cerebrovascular inflammation, for example, before CD4 positive T cells reactive to an antigen derived from the central nervous tissue are made to exist in the body of a non-human animal being under stress condition. On the other hand, if a drug having a treating effect is desired, administration of the test substance is performed after induction of cerebrovascular inflammation, for example, after CD4 positive T cells reactive to an antigen derived from the central nervous tissue are made to exist in the body of a non-human animal being under stress condition, or after the animal exhibits any disease or symptom.

The administration route of the test substance may be any of routes including intraperitoneal route, intravenous route, oral route, percutaneous rote, and other routes, and may be appropriately selected depending on qualities of the test substance, targeted disease or symptom, and the like. The dosage of the test substance and the vehicle to be used may be appropriately set and selected by those skilled in the art, with taking qualities and administration route of the test substance, and the like into consideration.

The step (iii) is a step in which development, progression, or occurrence of at least one disease or symptom selected from the group consisting of cerebrovascular inflammation, progressive multiple sclerosis, gastroenteritis, myocardial disorder, and sudden death is observed in the non-human animal to which the test substance is administered, and the observation results are compared with those in a non-human animal to which the test substance is not administered. In this step, if a reduction in or inhibition of development, progression, or occurrence of disease or symptom such as cerebrovascular inflammation, progressive multiple sclerosis, gastroenteritis, myocardial disorder, and sudden death, compared with those in a control animal in which the test substance is not administered, is observed in the non-human animal in which the test substance is administered, the test substance can be determined to have a preventing and/or treating effect for the disease or symptom.

Method for Determining Risk of Disease

Further aspect of the present invention relates to a method for determining the risk of a subject of being affected with or developing at least one disease or symptom selected from the group consisting of progressive multiple sclerosis, gastroenteritis, myocardial disorder, and sudden death, including, (a) a step of detecting the presence of inflammation at a blood vessel in the boundary area of the third ventricle, thalamus, and dentate gyrus, and (b) a step of determining that the subject has a high risk of being affected with or developing at least one disease or symptom selected from the group consisting of progressive multiple sclerosis, gastroenteritis, myocardial disorder, and sudden death when inflammation is detected in the step (a).

The step (a) is a step of detecting the presence of inflammation at a blood vessel in the boundary area of the third ventricle, thalamus, and dentate gyrus. Detection of inflammation can be performed by obtaining brain images of the subject non-invasively with conventional brain image acquisition means such as MRI, PET, or CT, and the like, and confirming the presence of findings indicating inflammation.

The step (b) is a step of determining that the subject has a high risk of being affected with or developing at least one disease or symptom selected from the group consisting of progressive multiple sclerosis, gastroenteritis, myocardial disorder, and sudden death when inflammation is detected in the step (a). The present inventors revealed that, when CD4 positive T cells reactive to an antigen derived from the central nervous tissue are made to exist in the body of a mouse being under stress condition, inflammation occurs at cerebral blood vessels, especially at specific blood vessels in the boundary area of the third ventricle, thalamus, and dentate gyrus, and this inflammation triggers various diseases and symptoms such as progressive multiple sclerosis, gastroenteritis, myocardial disorder, and sudden death. Accordingly, the presence of inflammation at the specific blood vessels described above can be utilized as an indicator for determining the risk of being affected with or developing these diseases or symptoms.

In the method of the present aspect, the subject whose risk to be determined is not limited, so long as being an animal to which being affected with or developing these diseases or symptoms matters. Typical examples of the subject include humans, and companion animals such as dogs and cats.

Pharmaceutical and Method for Preventing and/or Treating Diseases or Symptoms

As another aspect, the present invention also provides a pharmaceutical for preventing and/or treating at least one disease or symptom selected from the group consisting of progressive multiple sclerosis, gastroenteritis, myocardial disorder, and sudden death, including an antibody to CCL5, a GABA receptor agonist, an ATP receptor antagonist, a proton pump inhibitor, an antibody to LY6G6C, or an antibody to α2C adrenergic receptor, as an active ingredient.

The present inventors investigated the above-described phenomenon in which cerebrovascular inflammation induces diseases and the like by using the disease modeling animal of the present invention, and as the result, found the following mechanism. When a living body is stressed and becomes under stress condition, the sympathetic nerves are activated at its hypothalamic PVN, and noradrenaline is secreted at blood vessels existing in the boundary area of the third ventricle, thalamus, and dentate gyrus. Then, at the blood vessels, production of CCL5 and the like is enhanced, CD11b positive MHC class II-highly expressing cells and CD4 positive T cells are accumulated, and production and augmentation of inflammatory cytokines are enhanced, thereby inflammation is induced. Inflammation at these blood vessels activates the nerves in the dorsal medial hypothalamic nucleus (DMH) through ATP, which, through activation of the vagal nerves in the dorsal vagal nucleus (DMX) and nucleus tractus solitarii (NTS), further induces various diseases of the disease modeling animal such as progressive multiple sclerosis, gastroenteritis, myocardial disorder, and sudden death.

The present inventors furthermore found that, when stress is loaded, the expression of LY6G6C and α2C adrenergic receptor is enhanced at specific blood vessels existing in the boundary area of the third ventricle, thalamus, and dentate gyrus, and that, when antibodies to them are administered to the blood vessels, occurrence or progression of pathological conditions in the disease modeling animal is inhibited. While not wishing to be bound by any theory, since these antibodies exert the effects when directly administered to the blood vessels described above, these antibodies are presumed to inhibit reactions occurred at the specific blood vessels among a series of reactions starting from stress load, through induction of inflammation at the specific blood vessels, leading to occurrence of pathological conditions.

Based on the above mechanism, blocking a neural pathway of PVN—the above described blood vessels—DMH-DMX and NTS, suppressing secretion or inhibiting functions of neurotransmitters such as noradrenaline and ATP, suppressing secretion or inhibiting functions of CCL5 or inflammatory cytokines at the above described blood vessels, and inhibiting functions of LY6G6C or α2C adrenergic receptor, are considered to serve to prevent and/or treat various diseases or symptoms exhibited in the disease modeling animal. Accordingly, a substance and method to bring blocking the neural pathway described above, suppressing secretion or inhibiting functions of neurotransmitters described above, suppressing secretion or inhibiting functions of CCL5 or inflammatory cytokines, inhibiting functions of LY6G6C or α2C adrenergic receptor, are expected to be effective for preventing and/or treating, especially progressive multiple sclerosis, gastroenteritis, myocardial disorder, and sudden death, caused by stress load.

The above study further revealed that various diseases or symptoms exhibited in the disease modeling animal of the present invention are mutually related, and preventing and/or treating one disease or symptom will contribute to preventing and/or treating another disease or symptom. Accordingly, a substance or method for preventing and/or treating at least one disease or symptom selected from the group consisting of progressive multiple sclerosis, gastroenteritis, myocardial disorder, and sudden death, in the subject with cerebrovascular inflammation, is expected to be effective for preventing and/or treating other diseases or symptoms included in the group described above.

The antibody to CCL5 used in the present invention is not limited, so long as it can inhibit physiological functions of CCL5, and preferably is a neutralizing antibody that specifically binds to CCL5. The antibody to LY6G6C and the antibody to α2C adrenergic receptor are not limited as well, so long as they can inhibit physiological functions of LY6G6C or α2C adrenergic receptor, and preferably are neutralizing antibodies that specifically binds to LY6G6C and α2C adrenergic receptor, respectively. These antibodies can be monoclonal antibodies, chimeric antibodies, humanized antibodies, or human antibodies, and antibody fragments, such as Fab, Fab', or F(ab')2, of these antibodies can also be utilized. These antibodies can be prepared by common methods for antibody production, including immunizing a suitable laboratory animal such as a rabbit, mouse, and rat, preferably with recombinant CCL5, LY6G6C, or α2C adrenergic receptor, produced by genetic recombination technique, as an antigen. Alternatively, commercially available anti-CCL5 antibodies, anti-LY6G6C antibodies, and anti-α2C adrenergic receptor antibodies can be utilized.

The GABA receptor agonist used in the present invention is a substance that enhances physiological functions of a GABA receptor. While there are two types of GABA receptors: ionotropic $GABA_A$ receptors and metabotropic $GABA_B$ receptors, the GABA receptor agonist used in the present invention may be for any type. Preferably, the GABA receptor agonist is a $GABA_A$ receptor agonist.

Examples of the $GABA_A$ receptor agonist include, for example, benzodiazepines such as diazepam, midazolam, and flunitrazepam; non-benzodiazepines such as zolpidem, zopiclone, and eszopiclone; barbiturates such as phenobarbital, pentobarbital, and thiopental; quinazolinones such as methaqualone, etaqualone, and cloroqualone; phenols such as propofol; alcohols such as ethanol; neurostimulatory steroids such as allopregnanolone; piperidinediones: muscimol, and gaboxadol. Examples of the GABAs receptor agonist include, for example, baclofen. Furthermore, GABA, γ-hydroxybutyric acid, 1,4-butanediol, and the like, can be used as the GABA receptor agonist.

The ATP receptor antagonist used in the present invention is a substance that inhibits physiological functions of an ATP receptor. While ATP receptors can be largely divided into ionotropic receptors (P2X receptors) and G protein-coupled receptors (P2Y receptors), the ATP receptor antagonist used in the present invention may be for any type. Preferably, the ATP receptor antagonist is an antagonist for P2X receptors, examples of which include PPADS, decavanadate, A804598, brilliant blue G, A839977, A740003, and A438079.

The proton pump inhibitor used in the present invention is a substance that inhibits functions of a proton pump (hydrogen ion transporter). Examples of proton pump inhibitors include omeprazole, lansoprazole, sodium rabeprazole, and esomeprazole.

The substances described above, which are active ingredients of the pharmaceuticals according to the present invention, may be used as such as pharmaceuticals, or may be used in the form of pharmaceutical compositions containing other pharmaceutically acceptable ingredients including buffers, stabilizers, preservatives, excipients, and the like, and/or other active ingredients. Such pharmaceutical compositions are encompassed by the pharmaceuticals according to the present invention. Pharmaceutically acceptable ingredients are well known to those skilled in the art, and can be appropriately selected and used by those skilled in the art, within the scope of their ordinary implementation ability, for example from those described in the Japanese Pharmacopoeia, $17^{th}$ Edition or other written standards, depending on dosage forms.

The pharmaceutical according to the present invention can be in a suitable and known form. For example, the pharmaceutical according to the present invention may be in the form of parenteral formulations such as an injection and drip, or in the form of oral formulations optionally with a suitable coating. Examples of carriers that can be used for parenteral formulations include aqueous carriers such as saline, and isotonic solutions containing glucose, and D-sorbitol.

The method for administrating the pharmaceutical according to the present invention is not particularly limited, but when the pharmaceutical is a parenteral formulation, examples of the method include intravascular administration (preferably, intravenous administration), intraperitoneal administration, intracerebral administration, intrathecal administration, intestinal administration, and subcutaneous administration.

The dosage of the pharmaceutical according to the present invention is appropriately selected depending on the dosing regimen, the age of the patient, the disease conditions, other conditions, and the like. The pharmaceutical or pharmaceutical composition according to the present invention may be used in combination with another pharmaceutical beneficial for preventing and/or treating progressive multiple sclerosis, gastroenteritis, myocardial disorder, or sudden death.

Thus, the pharmaceutical according to the present invention can be used for preventing and/or treating at least one disease or symptom selected from the group consisting of progressive multiple sclerosis, gastroenteritis, myocardial disorder, and sudden death. Accordingly, the present invention also encompasses a method for preventing and/or treating at least one disease or symptom selected from the group consisting of progressive multiple sclerosis, gastroenteritis, myocardial disorder, and sudden death in a subject, including administrating an effective amount of an antibody to CCL5, GABA receptor agonist, ATP receptor antagonist, proton pump inhibitor, an antibody to LY6G6C, or antibody to α2C adrenergic receptor, to the subject in need thereof. Herein, the effective amount means an effective amount for preventing and/or treating the disease or symptom described above, and is appropriately determined depending on the dosing regimen, the age of the patient, the disease conditions, other conditions, and the like.

The prevention and/or treatment used herein covers every type of medically acceptable prophylactic and/or therapeutic intervention intended, for example, for cure, transient remission, or prevention of a disease or symptom. That is, the prevention and/or treatment of a disease or symptom covers medically acceptable intervention intended for various purposes, including retardation or stop of progression of the disease or symptom, regression or disappearance of lesion, prevention of development, or prevention of relapse.

The present invention further provides a method for preventing and/or treating at least one disease or symptom selected from the group consisting of progressive multiple sclerosis, myocardial disorder, and sudden death, including vagotomizing a subject in need thereof, as another aspect.

As described above, the present inventors revealed the involvement of DMX and NTS vagus nerves in the mechanism that cerebrovascular inflammation triggers diseases and the like. Therefore, blocking the neural pathway leading to the development of diseases with vagotomy brings the prevention and/or treatment of progressive multiple sclerosis, myocardial disorder, and sudden death.

A vagotomy is a surgical treatment for gastric ulcer and duodenal ulcer, and is known to include a truncal vagotomy in which the vagus anterior branch and the vagus posterior branch are dissected immediately below the diaphragm, a selective vagotomy in which hepatic branches, pyloric branches, and coeliac branches are preserved and only gastric branches are dissected, and a selective proximal vagotomy in which hepatic branches, pyloric branches, coeliac branches, and pylorus anterior and posterior branches are preserved and only gastric body branches are dissected. The vagotomy in the present invention may be any type of them, and is appropriately selected depending on the age of the patient, the disease conditions, other conditions, and the like.

The subject animal to which the pharmaceutical or the preventing method and/or treating method according to the present invention is performed, is an animal in which being affected with or developing these diseases or symptoms matters. Typical examples of the subject include humans, and companion animals such as dogs and cats, and livestock animals such as cows and pigs.

The present invention will be further described in detail with following Examples, to which the present invention is not limited.

EXAMPLES

Animals and Reagents

C57BL/6 mice were purchased from Japan SLC, Inc., C57BL/6-PL mice were purchased from Taconic Biosciences, Inc., CX3CR1$^{CreER}$ ROSA26-TdTomato mice were given from Professor Marco Prinz at Freiburg University. All of them were bred under SPF conditions. All animal experiments were performed under approval of the Institutional Animal Care and Use Committee of Hokkaido University.

The following antibodies were used for the flow cytometry analysis:

FITC-conjugated anti-CD19 antibody (eBioscience), anti-CD11b antibody (eBioscience), anti-CD44 antibody (eBioscience), anti-CD4 antibody (eBioscience), PE-conjugated anti-CD44 antibody (eBioscience), anti-TCR antibody (eBioscience), PE-Cy7-conjugated anti-CD90.2 antibody (eBioscience), APC-conjugated anti-CD4 antibody (BioLegend), anti-I-A/I-E antibody (BioLegend), biotin-conjugated anti-CD11b antibody (eBioscience), anti-CD19 antibody (eBioscience), anti-NK1.1 antibody (eBioscience), anti-CD11c antibody (eBioscience), and anti-TCR antibody (eBioscience).

The following antibodies were used for immunohistochemistry:

FITC-conjugated anti-I-A/I-E antibody (BioLegend), anti-dopamine transporter antibody (Abcam plc.), anti-noradrenaline transporter antibody (Abcam plc.), anti-phosphorylated CREB antibody (Cell Signaling Technology, Inc.), anti-tyrosine hydroxylase antibody (Abcam plc.), anti-phosphorylated c-Fos (Ser32) (Cell Signaling Technology, Inc.), control rabbit IgG (DA1E) (Cell Signaling Technology, Inc.), biotin-conjugated anti-CD4 antibody (BioLegend), anti-CD11b antibody (eBioscience), anti-I-A/I-E antibody (BioLegend), anti-*Phaseolus vulgaris* agglutinin antibody (VECTOR, Inc.), anti-CD31 antibody (Abcam plc.), anti-activated caspase3 antibody (Cell Signaling Technology, Inc.), anti-CHT1 antibody (produced by Department of Anatomy and Embryology, Graduate School of Medicine, Hokkaido University), Alexa Fluor 546 donkey anti-goat IgG antibody (H+L), Alexa Fluor 488 goat anti-rabbit IgG antibody (H+L), Alexa Fluor 546 goat anti-rabbit IgG antibody (H+L), Alexa Fluor 647 goat anti-rabbit IgG antibody (H+L), Alexa Fluor 647 goat anti-chicken IgG antibody (Invitrogen), and streptavidin Alexa Fluor 546 conjugate (Invitrogen).

In in vivo neutralization tests, the following antibodies were used:

Anti-mouse IL-17 antibody and anti-CCL5 antibody (both from R&D Systems, Inc.), anti-IFN-γ antibody (purified according to Ueda et al. (2006), Int. Immunol., 18, 1397-1404).

6-hydroxydopamine hydrochloride (6-OHDA), lansoprazole, FITC-conjugated cholera toxin B subunit (FITC-CTB), tamoxifen, and ATP were purchased from Sigma-Aldrich Co. LLC. PHA-L was purchased from VECTOR, Inc. A438079 was purchased from TOCRIS Bioscience.

Test Data and Statistical Analysis

All tests included in Examples were performed at least three times, and the representative data was shown as the results. In each graph, mean scores ±standard deviation are shown. Student's t-tests (two tailed) were used for the statistical analysis of differences between two groups, and analysis of variance tests were used for the statistical analysis of differences among three or more groups. p values less than 0.05 were considered to be statistically significant, and were denoted in graphs by *$p<0.05$, $p<0.01$, or *$p<0.001$.

Example 1 Production of Disease Modeling Mice (1) Disease Modeling Mice Produced by Induction of Sleep Disorder (i) Stress Load Loading PAWW stress and induction of sleep disorder thereby were performed as described previously (Miyazaki, K. et al., PloS one, 2013, 8, e55452). 6-8 weeks old C57BL/6 mice were individually maintained in plastic cages with running wheels for habituation. Then, through loading PAWW stress by replacing wood beddings in the cages with water having depth of 1.5 cm to make the mice exercise continuously on the wheel for 2 days, sleep disorder was induced in the mice.

(ii) Preparation of EAE-Pathogenic CD4 Positive T Cells

Preparation and transfer of EAE-pathogenic CD4 positive T cells were performed as described previously (Arima, Y. et al., Cell., 2012, 148, 447-457; Arima, Y. et al., eLife, 2015, 4, e08733; Ogura, H. et al., Immunity, 2008, 29, 628-636). Briefly, C57BL/6 mice were injected subcutaneously with a MOG (35-55) peptide (Sigma-Aldrich Co. LLC.) together with complete Freund's adjuvant (Sigma-Aldrich Co. LLC.) at the base of the tail, then 0, 2, and 7 days after MOG peptide injection, the mice were further injected intravenously with pertussis toxin (Sigma-Aldrich Co. LLC.). 9 days after MOG peptide injection, lymphocytes were collected from the spleens of the mice, sorted with anti-CD4 microbeads (Miltenyi Biotec, Inc.) to obtain a cell population rich in CD4 positive T cells. The resulting cell population ($4\times10^6$ cells) was co-cultured with MOG peptide-pulsed irradiated spleen cells ($1\times10^7$ cells) for 2 days in the presence of rIL-23 (10 ng/mL; R & D Systems, Inc.). Cells were collected from the culture medium, enriched with the anti-CD4 microbeads, and EAE-pathogenic CD4 positive T cells were prepared.

(iii) Transfer of EAE-Pathogenic CD4 Positive T Cells 2 days after starting stress load described in (i) above, the EAE-pathogenic CD4 positive T cells ($1.5\times10^7$ cells) prepared in (ii) above were transferred to the mice by intravenous injection to produce disease modeling mice. Also, mice into which EAE-pathogenic CD4 positive T cells were transferred without stress load, mice into which EAE-pathogenic CD4 positive T cells were not transferred after stress load, mice without stress load and without EAE-pathogenic CD4 positive T cells transfer, were prepared.

(2) Disease Modeling Mice Produced by Wet Bedding Stress

Disease modeling mice were prepared in the same way as described in (1) above, except that stress was loaded by wet bedding instead of induction of sleep disorder. Wet bedding stress was loaded by placing 350 mL/cage of water into cages with wood beddings to make the beddings wet, and maintaining 6-8 weeks old C57BL/6 mouse in this cage for 2 days. Wet beddings were exchanged daily.

The following tests were performed with three to five mice per each group.

Example 2 Analysis of Pathological Conditions of Disease Modeling Mice (1) EAE Pathological conditions of EAE in the mice prepared in Example 1 were evaluated with clinical score. Clinical score was determined as described previously (Arima, Y. et al., Cell, 2012, 148, 447-457; Arima, Y. et al., eLife, 2015, 4, e08733; Ogura, H. et al., Immunity, 2008, 29, 628-636). Clinical scores represent the severity of encephalomyelitis symptoms, and the scores increase with increasing the severity. A score of 0 is equivalent to normal state without abnormal findings, and a score of 5 is equivalent to death.

Changes over time of clinical scores of the mice in which sleep disorder was induced in Example 1 (1) are shown in FIG. 1A, and their mortality 10 days after EAE-pathogenic CD4 positive T cell transfer are shown in FIG. 1B. In the untreated mice group (SD– T cells–) and the mice group in which sleep disorder was induced but EAE-pathogenic CD4 positive T cells were not transferred (SD+ T cells–), the clinical scores were not elevated, i.e. remained 0. In the mice group in which sleep disorder was induced followed by transfer of EAE-pathogenic CD4 positive T cells (SD+T cells+), the clinical scores rapidly increased on the $7^{th}$ day after transfer, and the mice exhibited high mortality. In contrast, in the mice group received transfer of EAE-pathogenic CD4 positive T cells alone (SD-T cells+), the clinical scores slowly increased but no death case was observed.

Figure 2:
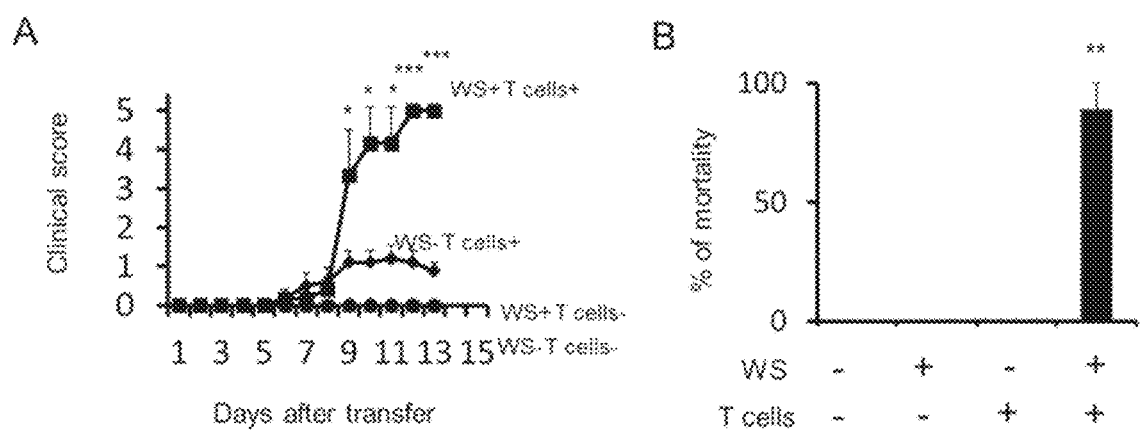
FIG. 2 illustrates graphs indicating pathological conditions of mice on which wet bedding stress was loaded followed by transfer of EAE-pathogenic CD4 positive T cells (WS+ T cells+), mice into which EAE-pathogenic CD4 positive T cells were transferred without wet bedding stress load (WS− T cells+), mice which underwent wet bedding stress load alone (WS+ T cells−), and mice with neither treatment (WS− T cells−) in Example 1 (2).

The clinical scores and mortality of the mice on which wet bedding stress was loaded in Example 1 (2) exhibited a similar tendency to those of the mice in which sleep disorder was induced (FIGS. 2A and 2B, WS+ T cells+). In the mice into which, instead of EAE-pathogenic CD4 positive T cells, CD4 positive T cells reactive to antigens not derived from the central nerve tissue such as ovalbumin were transferred after stress load, a rapid increase in clinical scores was not observed (data not shown).

Thus, it was confirmed that mice into which, under stress condition, EAE-pathogenic CD4 positive T cells were transferred have pathogenic conditions of progressive multiple sclerosis and sudden death characterized by a rapid increase in clinical scores.

Figure 3:
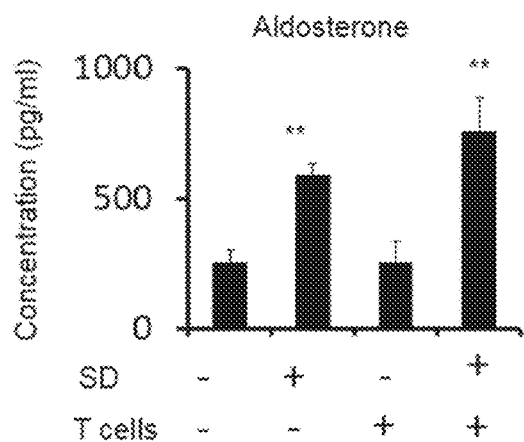
FIG. 3 is a graph showing serum aldosterone levels of each mice groups in Example 1 (1) 9 days after EAE-pathogenic CD4 positive T cell transfer.

Furthermore, blood was collected from the mice produced in Example 1 (1) on 9 days after the transfer of EAE-pathogenic CD4 positive T cells, and blood aldosterone levels were measured with ELISA kit (ENDOCRINE). Since sleep disorder increased blood aldosterone levels regardless of transferring EAE-pathogenic CD4 positive T cells (FIG. 3), the activation of hypothalamic-pituitary-adrenal axis by stress load was suggested.

(2) Gastroenteritis

Pathological conditions of gastroenteritis in the mice prepared in Example 1 (1) were evaluated on 10 days after the transfer of EAE-pathogenic CD4 positive T cells. Stools collected from each mouse were suspended in saline (20 mL/g stool), the supernatants obtained by centrifugation (8000 rpm, 5 minutes) were diluted to 10 times with saline, and fecal occult blood test was performed with Hemastix (Registered) (Siemens Healthcare Pty, Ltd.). Bloody stool scores were calculated according to the scoring method described on the package of Hemastix.

Figure 4:
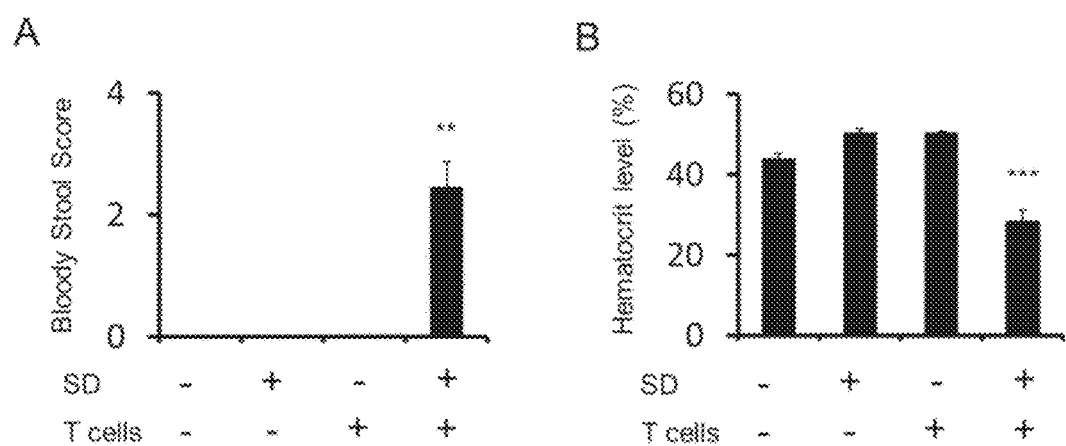
FIG. 4 illustrates graphs indicating gastroenteritis conditions of each mice groups in Example 1 (1).

The results are shown in FIG. 4. Bloody stools were found only in the mice group in which sleep disorder was induced followed by transfer of EAE-pathogenic CD4 positive T cells (SD+ T cells+), and hematocrits were decreased correspondingly in this mice group.

Figure 5:
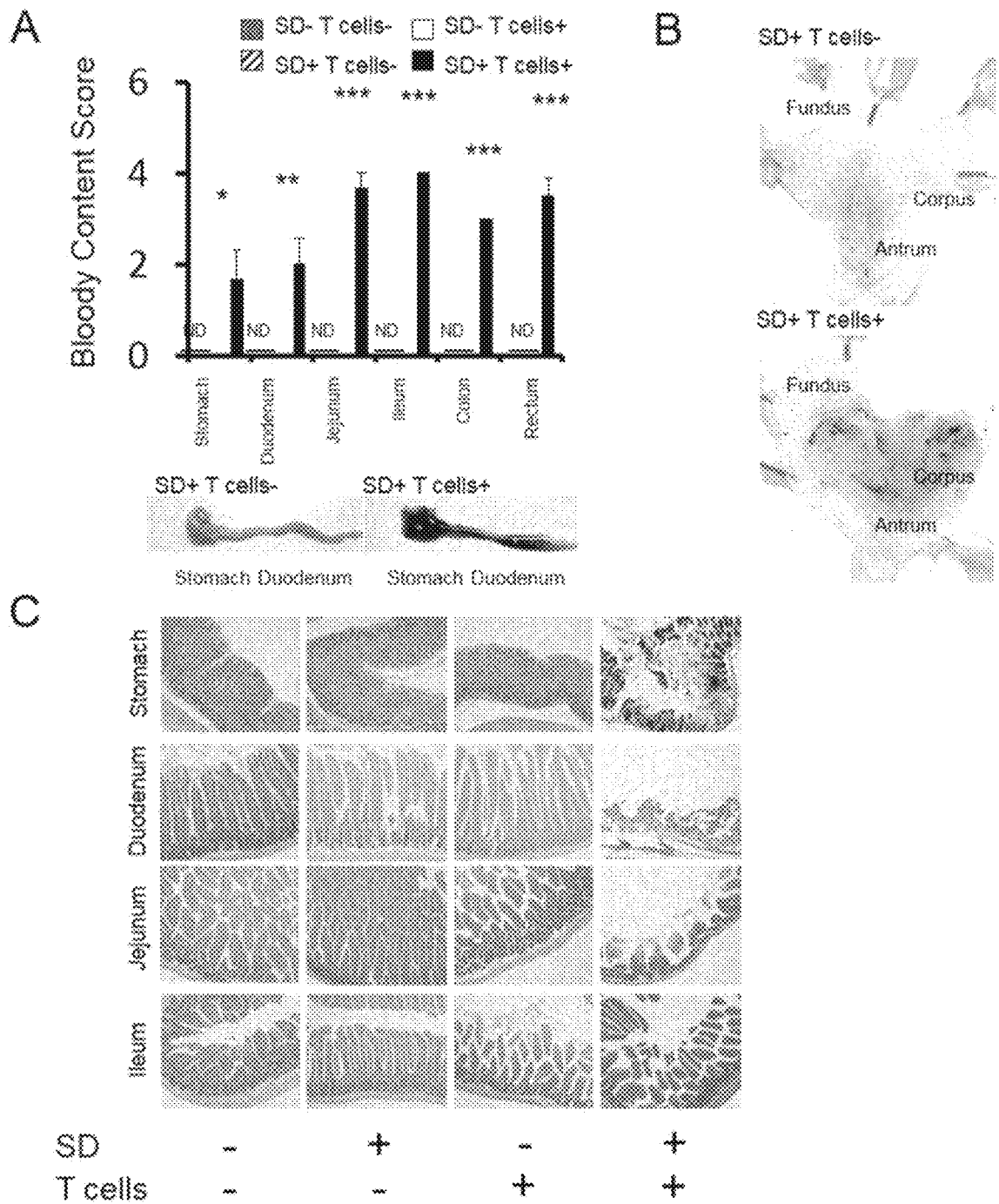
FIG. 5 illustrates graphs indicating gastroenteritis conditions of each mice groups in Example 1 (1).

Each part of the digestive tract (stomach, duodenum, jejunum, ileum, colon, rectum) was washed with 1 mL of saline, and blood contents of the washings were determined in the same way as in the fecal occult blood test. In the mice group in which sleep disorder was induced followed by transfer of EAE-pathogenic CD4 positive T cells, bleedings in the stomach and the upper parts of the intestine were seen (FIG. 5A). In this mice group, focal bleeding lesions were detected in the stomach (FIG. 5B, black points), and inflammations in epithelial tissues of the stomach and duodenum were found (FIG. 5C).

Figure 6:
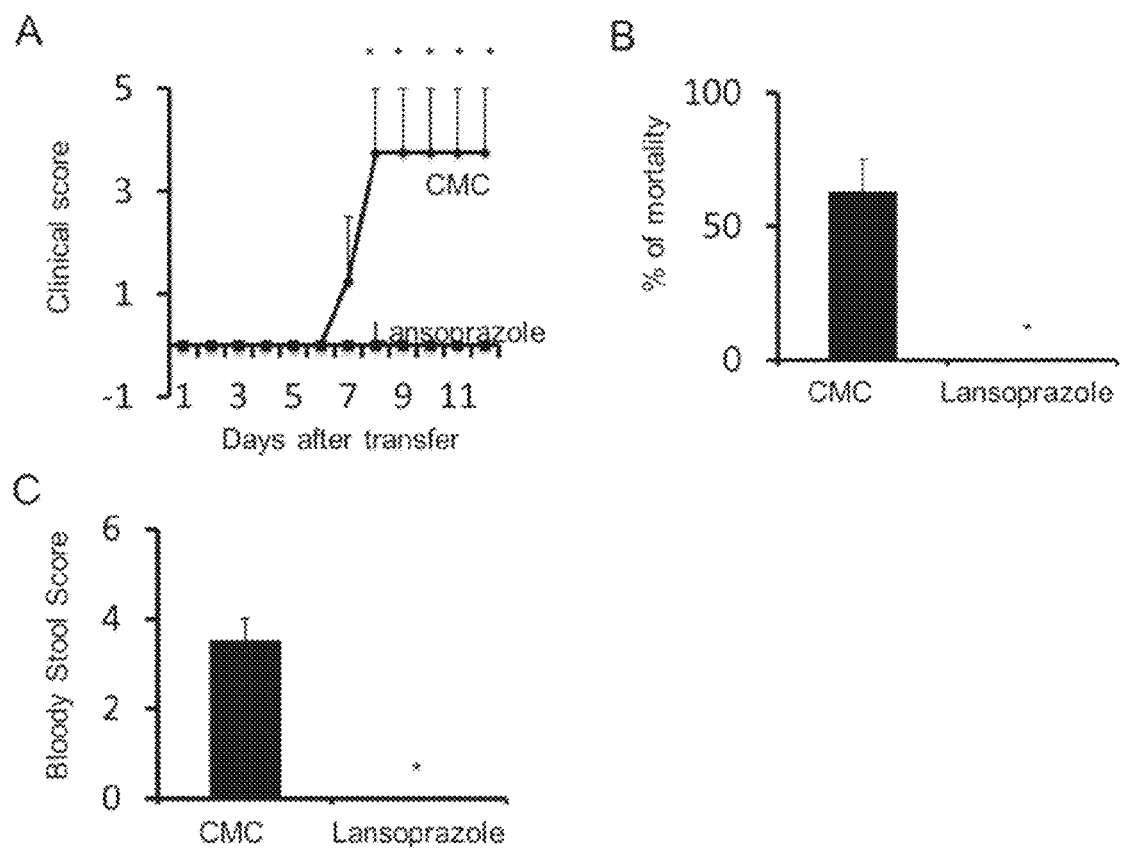
FIG. 6 illustrates graphs indicating pathological conditions of mice in which sleep disorder was induced followed by transfer of EAE-pathogenic CD4 positive T cells, when lansoprazole was administered to the mice.

Then, to the mice in which sleep disorder was induced followed by transfer of EAE-pathogenic CD4 positive T cells, a proton pump inhibitor, lansoprazole, or a control, carboxymethyl cellulose (CMC), at a dose of 30 mg/kg body weight was orally administered daily after transferring EAE-pathogenic CD4 positive T cells. In the mice in which sleep disorder was induced followed by transfer of EAE-pathogenic CD4 positive T cells, lansoprazole remarkably reduced clinical scores, the mortality 10 days after the transfer, and bloody stool scores (FIG. 6).

Thus, it was confirmed that mice into which, under stress condition, EAE-pathogenic CD4 positive T cells were transferred have pathogenic conditions of gastroenteritis characterized by inflammation and bleeding in the stomach and the upper parts of the intestine, and that a proton pump inhibitor, lansoprazole, improves clinical scores and pathogenic conditions of gastroenteritis, and reduces mortality.

(3) Myocardial Disorder

Figure 7:
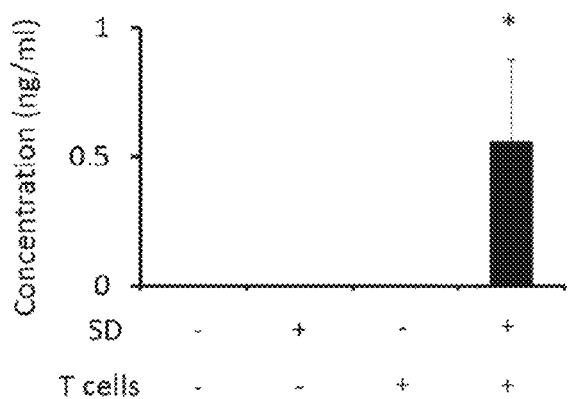
FIG. 7 is a graph showing serum troponin I levels of each mice groups in Example 1 (1) 9 days after EAE-pathogenic CD4 positive T cell transfer.
Figure 8:
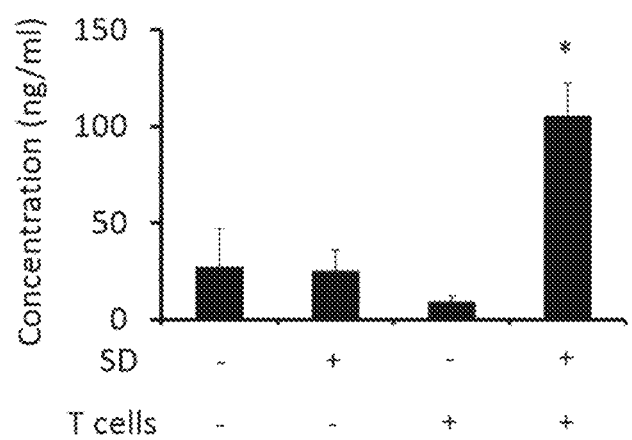
FIG. 8 is a graph showing serum creatine kinase MB levels of each mice groups in Example 1 (1) 9 days after EAE-pathogenic CD4 positive T cell transfer.

Pathological conditions of myocardial disorder in the mice prepared in Example 1 (1) were evaluated. Blood was collected 9 days after the transfer of EAE-pathogenic CD4 positive T cells, and blood troponin I levels were measured with ELISA kit (Life diagnotics, Inc.), and blood creatinine kinase MB levels were measured with ELISA kit (Lifespan BioSciences, Inc.). Blood troponin I levels (FIG. 7) and blood creatinine kinase MB levels (FIG. 8) were increased in the mice into which, under stress condition, EAE-pathogenic CD4 positive T cells were transferred, and it was suggested that the mice have pathological conditions of myocardial disorder characterized by cell death in the heart. By electrocardiography, signs of heart failure were detected in this mice group (data not shown).

Figure 9:
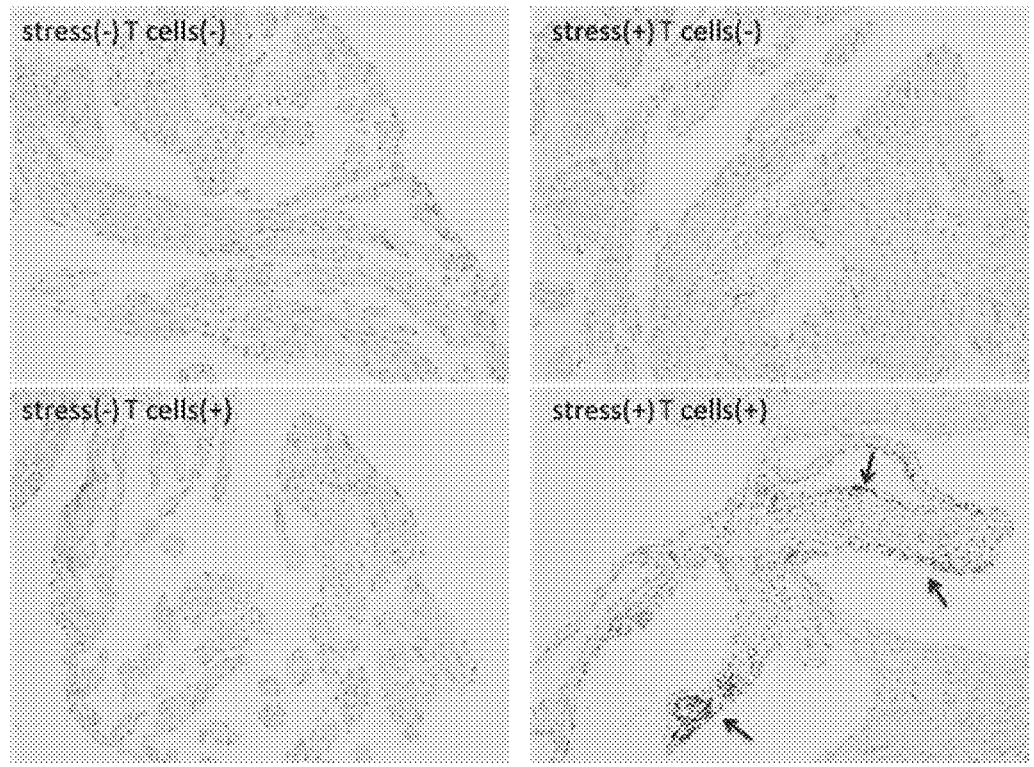
FIG. 9 illustrates photographs of immunostained hearts of each mice groups in Example 1 (1) with an anti-activated caspase-3 antibody.
Figure 9:
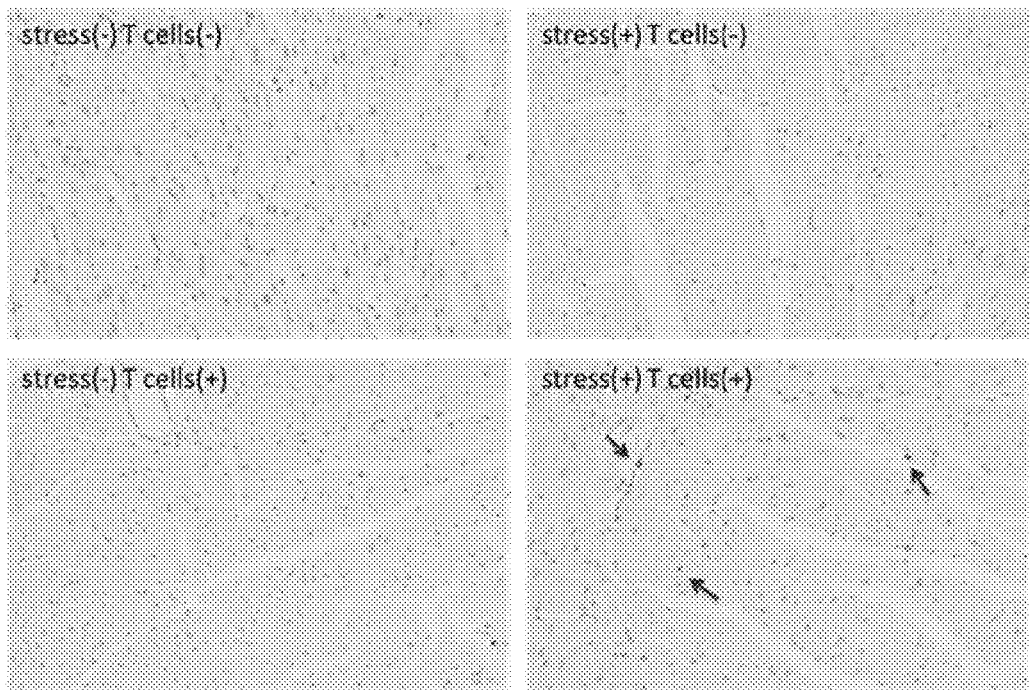

In addition, by immunohistochemistry using an anti-activated caspase-3 antibody, an increase in apoptosis was observed in the heart of the mice group in which sleep disorder was induced followed by transfer of EAE-pathogenic CD4 positive T cells, and the tendency to increase apoptosis was more remarkable in the upper heart parts (FIG. 9, indicated by arrows).

Figure 10:
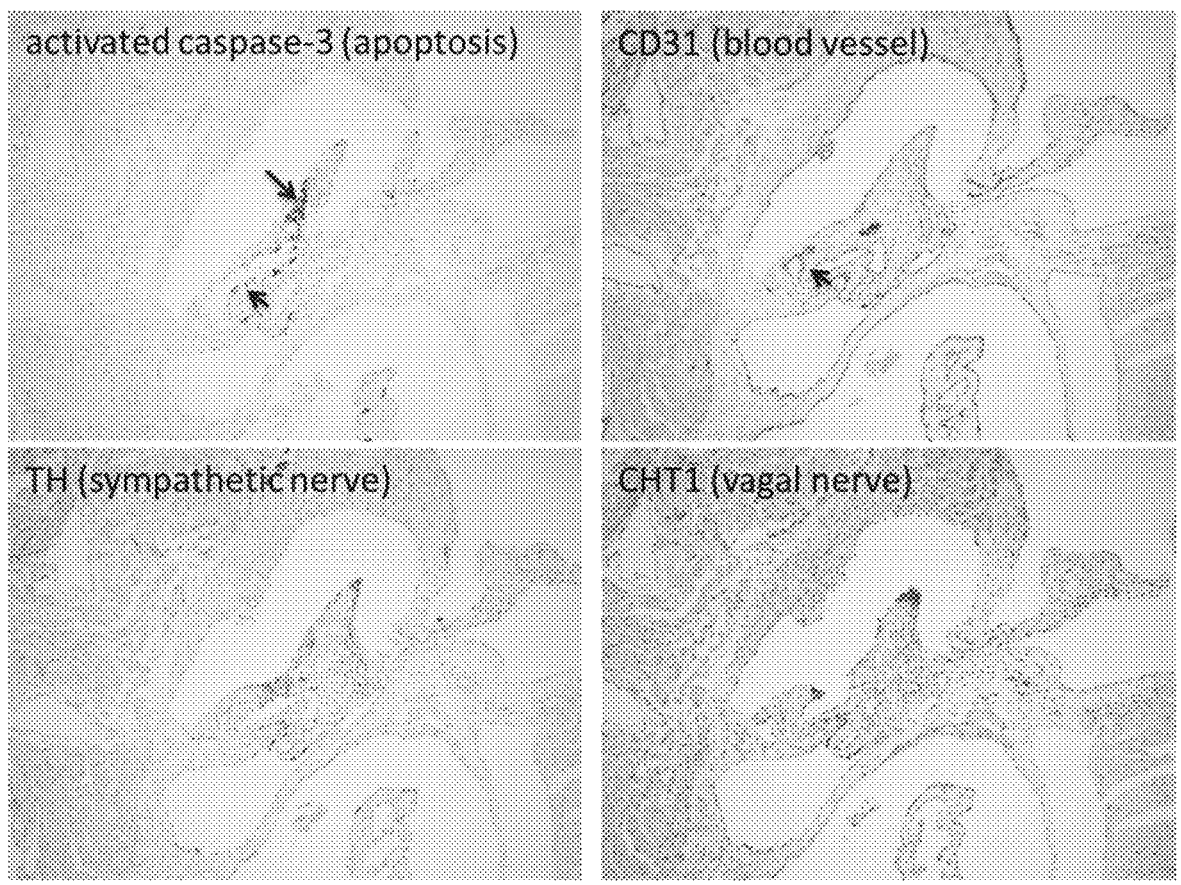
FIG. 10 illustrates photographs of immunostained upper heart parts of mice in which sleep disorder was induced followed by transfer of EAE-pathogenic CD4 positive T cells. The immunostaining was performed with each of an anti-activated caspase-3 antibody, anti-CD31 antibody, anti-tyrosine hydroxylase antibody (TH), and anti-choline transporter 1 antibody (CHT1).

The upper heart parts of the disease modeling mice in which sleep disorder was induced followed by transfer of EAE-pathogenic CD4 positive T cells were stained immunohistochemically with each antibody for an apoptosis marker of activated caspase-3, a blood vascular marker of CD31, a sympathetic nerve marker of tyrosine hydroxylase, and a vagal nerve marker of choline transporter 1. The immunostained images are shown in FIG. 10. The part intensely stained with an anti-activated caspase-3 antibody (FIG. 10, upper left-sided photograph, part indicated by upper arrow) was structurally estimated to be the valve. The part stained with an anti-CD31 antibody (FIG. 10, upper right-sided photograph, part indicated by arrow) was also stained with an anti-activated caspase-3 antibody (FIG. 10, upper left-sided photograph, part indicated by lower arrow), and it was considered that apoptosis also occurs in the blood vessel. Moreover, since the surrounding area of the anti-activated caspase-3 antibody-stained part was also stained with an anti-tyrosine hydroxylase antibody, and anti-choline transporter 1 antibody, it was suggested that neural activity is involved with apoptosis of cardiac cells.

Thus, it was confirmed that mice into which, under stress condition, EAE-pathogenic CD4 positive T cells were transferred have pathogenic conditions of myocardial disorder characterized by cell death in the heart.

(4) Local Inflammation at the Specific Intracerebral Blood Vessels

Accumulation of MHC class II positive cells and CD4 positive T cells in the mice prepared in Example 1 (1) was investigated. The fifth lumbar vertebra and the brain were removed from the mice 10 days after transferring EAE-pathogenic CD4 positive T cells, embedded in SCEM (SECTION-LAB Co., Ltd.), and sliced to sections with a thickness of 10 μm using a microtome device, CM3050 (Leica Microsystems GmbH). Sections were collected using Cryofilm type IIIC (16UF) (SECTION-LAB Co., Ltd.), subjected to hematoxylin eosin staining, or to immunohistochemical staining with an anti-MHC class II antibody or anti-CD4 antibody, and analyzed by BZ-9000 microscope (KEYENCE Corporation) using HS ALL software in BZ-II analyzer (KEYENCE Corporation).

Figure 11:
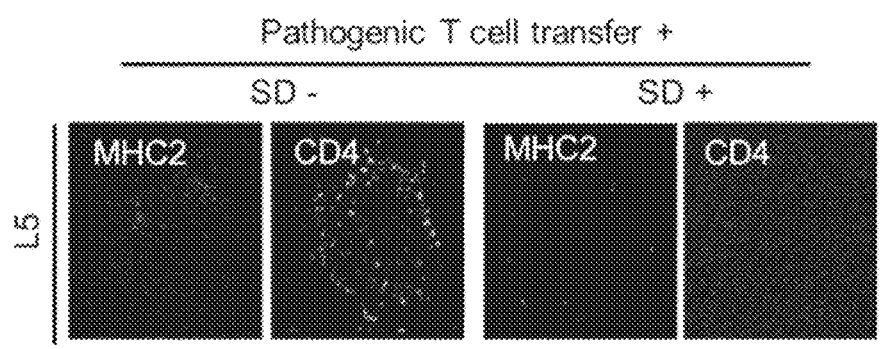
FIG. 11 illustrates photographs of the immunostained fifth lumbar cords of mice into which EAE-pathogenic CD4 positive T cells were transferred without or with induction of sleep disorder, wherein the immunostaining was performed with an anti-MHC class II antibody or anti-CD4 antibody (FIG. 11A); and a graph showing the stained cell numbers (FIG. 11B).
Figure 11:
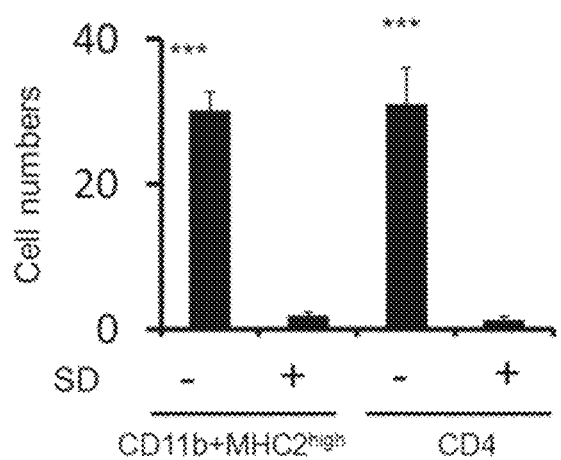
Figure 12:
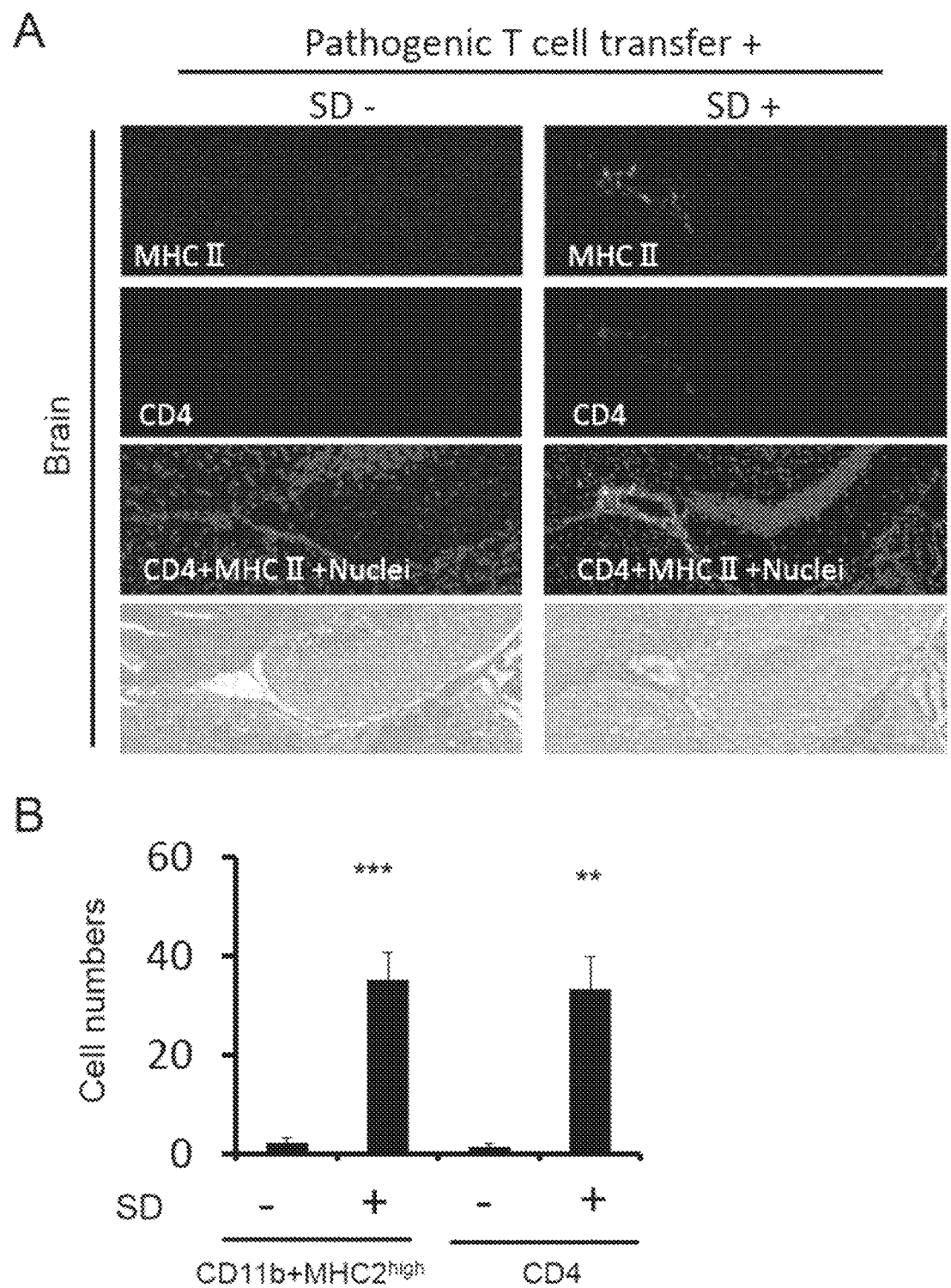
FIG. 12 illustrates photographs of the immunostained third ventricular regions of mice into which EAE-pathogenic CD4 positive T cells were transferred without or with induction of sleep disorder, wherein the immunostaining was performed with an anti-MHC class II antibody or anti-CD4 antibody (FIG. 12A); and a graph showing the stained cell numbers (FIG. 12B).

In the mice group underwent transfer of EAE-pathogenic CD4 positive T cells alone (SD−), MHC class II positive cells and CD4 positive T cells were accumulated at dorsal blood vessels in the fifth lumbar vertebra, as previously reported (Arima et al., (2012) Cell, 148, 447-457) (FIG. 11). In contrast, in the mice group in which sleep disorder was induced followed by transfer of EAE-pathogenic CD4 positive T cells (SD+), both of MHC class II positive cells and CD4 positive T cells were found to be accumulated at specific blood vessels in the boundary area of the third ventricle, thalamus, and dentate gyrus (FIG. 12). Various immune cells such as CD8 positive T cells, B cells, NK cells, and neutrophils were also accumulated at these blood vessels (data not shown).

Furthermore, brains were removed from the mice 9 days after transferring EAE-pathogenic CD4 positive T cells, dissected into each parts of the cerebellum and brain stem, cortex, and hippocampus and interbrain, and enzymatically digested with Neural Tissue Dissection kit (Miltenyi Biotec Company) to prepare single cell suspension. $10^6$ cells in the suspension were incubated with a fluorescent conjugated antibody on ice for 30 minutes, and the surface of the cells was labelled. Then, the cells were analyzed using CyAn flow cytometer (Beckman Coulter Corporation), and the obtained data were analyzed using Summit software (Beckman Coulter Corporation) or FlowJo software (Tree Star, Inc.).

Figure 13:
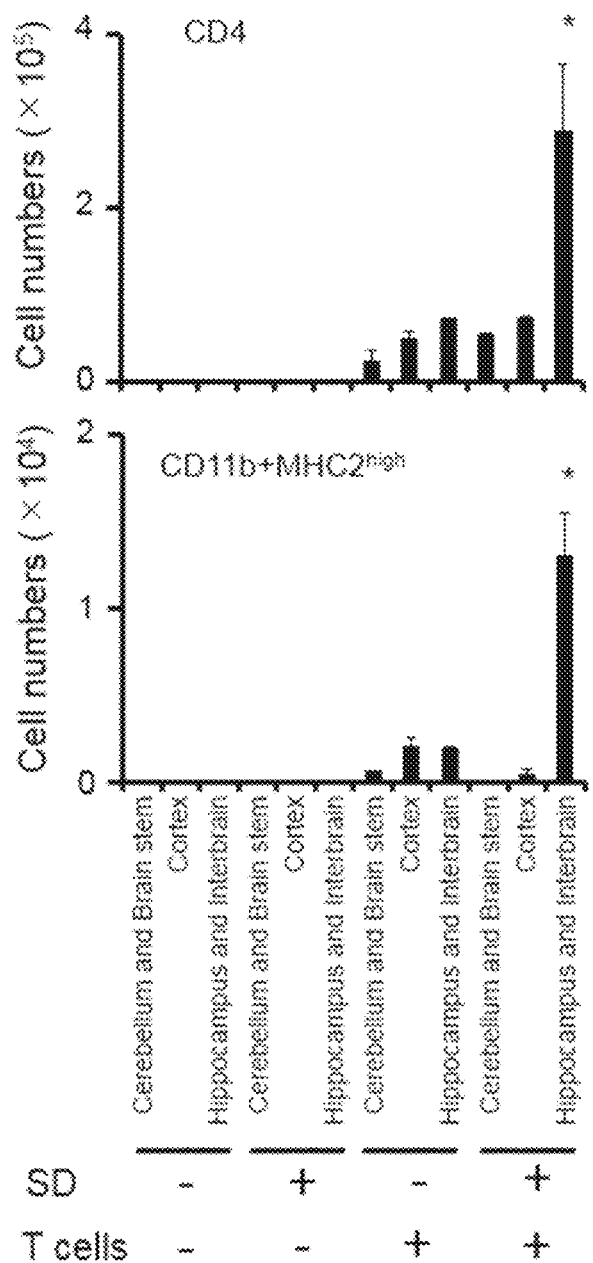
FIG. 13 illustrates graphs showing the numbers of CD11b positive MHC class II-highly expressing cells and CD4 positive T cells of each mice groups in Example 1 (1) in various brain parts.

Flow cytometry analysis results of CD11b positive MHC class II-highly expressing cells and CD4 positive T cells existing in various parts of the brain are shown in FIG. 13. In the mice group in which sleep disorder was induced followed by transfer of EAE-pathogenic CD4 positive T cells (SD+ T cells+), the MHC class II-highly expressing cells and CD4 positive T cells were remarkably accumulated to the hippocampus and interbrain where the specific blood vessels are located.

Then, in order to investigate the origin of the MHC class II-highly expressing cells accumulated in the hippocampus and interbrain, disease modeling mice were produced by induction of sleep disorder in the same way as in the Example 1 (1), using CX3CR1$^{CreER}$ ROSA26-TdTomato mice instead of C57BL/6 mice. Tamoxifen at a dose of 2 mg/mouse was orally administered to the mice for two successive days to express Td-Tomato, then, six weeks after the administration, EAE-pathogenic CD4 positive T cells were transferred into the mice. 10 days after the transfer, the hippocampi and interbrains were removed from the mice, and the expression of Td-Tomato in MHC class II-highly expressing cells was analyzed by flow cytometry.

Figure 14:
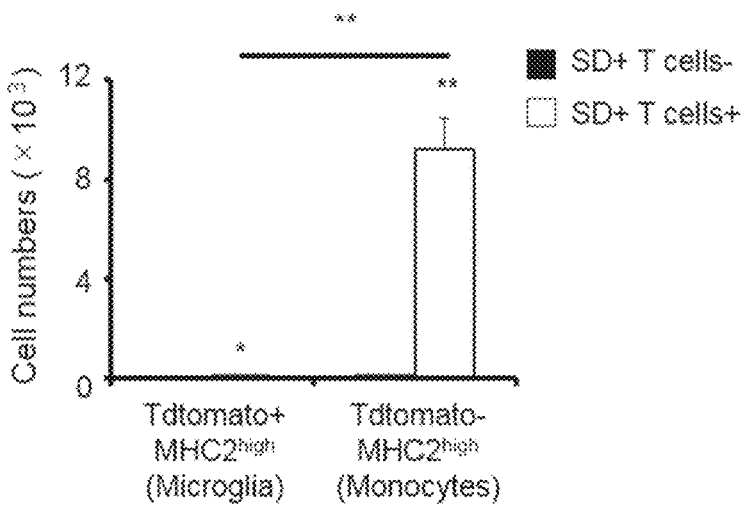
FIG. 14 is a graph showing the numbers of microglia cells and monocytes in the hippocampi and interbrains of CX3CR1$^{CreER}$ ROSA26-TdTomato mice in which sleep disorder was induced followed by transfer of EAE-pathogenic CD4 positive T cells.

The results are shown in FIG. 14. In the hippocampi and interbrains of mice in the group in which sleep disorder was induced followed by transfer of EAE-pathogenic CD4 positive T cells (SD+ T cells+), Td-Tomato negative cells, that is, peripheral organ-derived MHC class II-highly expressing cells (monocytes) were highly accumulated, while Td-Tomato positive cells, that is, central organ-derived MHC class II-highly expressing cells (microglia cells) were slightly accumulated.

Thus, it was confirmed that mice into which, under stress condition, EAE-pathogenic CD4 positive T cells were transferred have pathogenic conditions of inflammation characterized by accumulation of immune cells such as MHC class II-highly expressing cells and CD4 positive T cells, at the specific blood vessels in the boundary area of the third ventricle, thalamus, and dentate gyrus.

Example 3 Functional Analysis of CCL5 and Inflammatory Cytokines in Disease Modeling Mice (1) CCL5

To the mice produced in Example 1 (1) in which sleep disorder was induced followed by transfer of EAE-pathogenic CD4 positive T cells, an anti-CCL5 antibody or a control rat IgG antibody (100 μg/mouse each) was intraperitoneally injected daily after transferring EAE-pathogenic CD4 positive T cells, and pathogenic conditions of EAE was evaluated in the same way as in the Example 2 (1). In addition, cell accumulation at the specific blood vessels in the mice 10 days after the transfer of EAE-pathogenic CD4 positive T cells was investigated in the same way as in the Example 2 (4).

Figure 15:
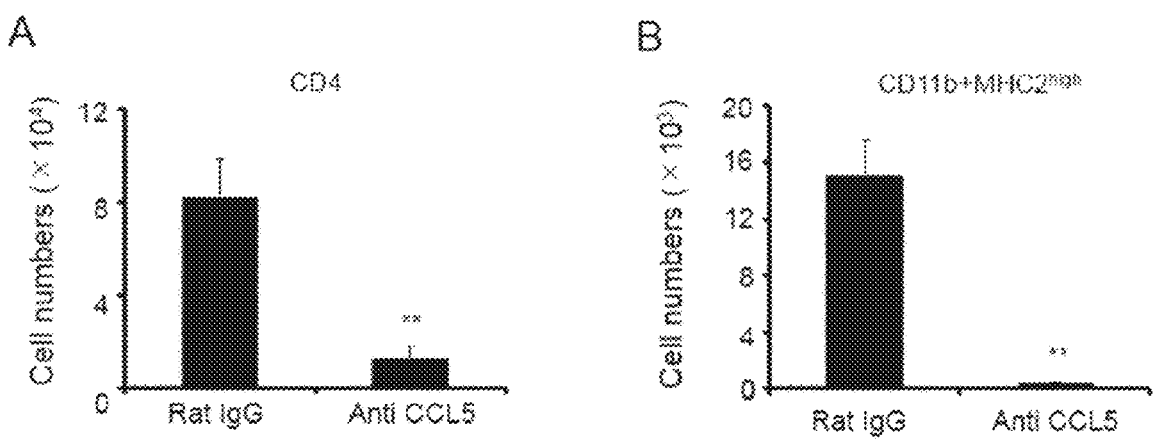
FIG. 15 illustrates a graph showing the numbers of CD4 positive T cells (FIG. 15A) and CD11b positive MHC class II-highly expressing cells (FIG. 15B) in the hippocampi and interbrains of mice in which sleep disorder was induced followed by transfer of EAE-pathogenic CD4 positive T cells, when an anti-CCL5 antibody or a rat IgG antibody, control, was administered to the mice.
Figure 16:
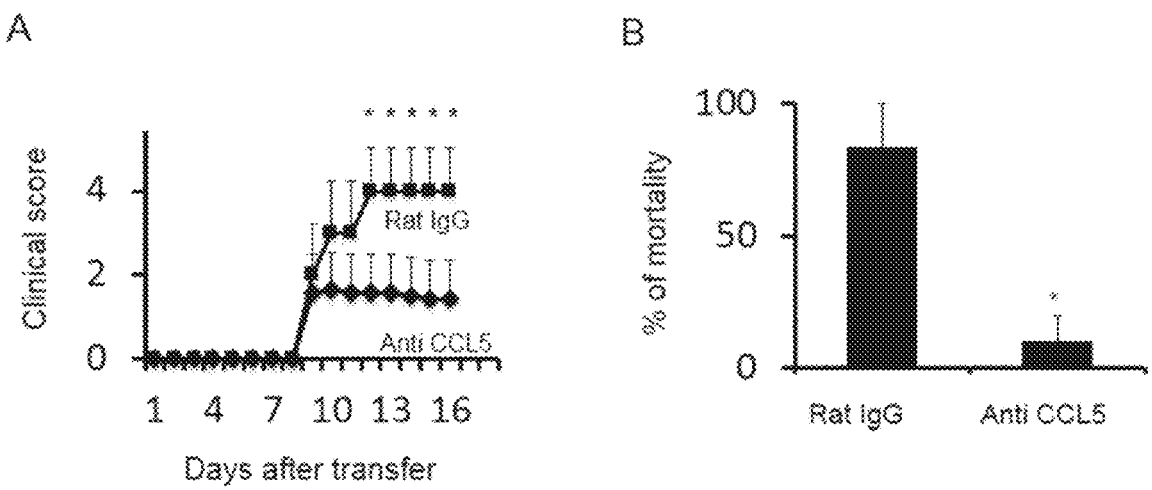
FIG. 16 illustrates graphs indicating pathological conditions of mice in which sleep disorder was induced followed by transfer of EAE-pathogenic CD4 positive T cells, when an anti-CCL5 antibody or a rat IgG antibody, control, was administered to the mice.

The anti-CCL5 antibody suppressed accumulation of CD4 positive T cells and CD11b positive MHC class II-highly expressing cells at the specific blood vessels (FIG. 15), and reduced clinical scores and mortality (FIG. 16). In contrast, antibodies to other chemokines such as CCL2 and CX3CL1 did not show such effects (data not shown).

The expression level of a chemokine, CCL5, at the specific blood vessels was measured as follows. Approximately 100 frozen sections (a thickness of 15 μm) were prepared from the mice 4 days after the transfer of EAE-pathogenic CD4 positive T cells by using the same method as in Example 2 (4), fixed with PAXgene (QIAGEN Inc.) for 15 minutes, then with 100% EtOH for 10 minutes. Tissues around the blood vessels in the third ventricular region in the section were collected with a laser microdissection device, DM6000B (Leica Microsystems Inc.), and total RNA was extracted with RNeasy micro kit (QIAGEN Inc.). The extracted RNA was treated with DNase and a reverse transcription reaction was performed to obtain cDNA.

The obtained cDNA was subjected to real-time qPCR analysis with GeneAmp 5700 sequence detection system (ABI) and KAPA PROBE FAST ABI Prism qPCR kit (Kapa Biosystems, Inc.) to measure the expression levels of CCL5 and an internal control gene HPRT. The PCR primer pairs and primers used were as follows:
mouse HPRT primers;
5'-AGCCCCAAAATGGTTAAGGTTG-3' (SEQ ID NO: 1) and
5'-CAAGGGCATATCCAACAACAAAC-3' (SEQ ID NO: 2);
mouse HPRT probe;
5'-ATCCAACAAAGTCTGGCCTGTATCCAACAC-3' (SEQ ID NO: 3);
mouse CCL5 primers;
5'-CTCCCTGCTGCTTTGCCTAC-3' (SEQ ID NO: 4) and
5'-CGGTTCCTTCGAGTGACAAACA-3' (SEQ ID NO: 5);

Mouse CCL5 probe;
5'-TGCCTCGTGCCCACGTCAAGGAGTATT-3' (SEQ ID NO: 6).

The condition of real-time PCR was 50° C. 2 minutes, 95° C. three minutes, followed by 40 cycles of 95° C. three seconds and 60° C. 30 seconds.

Figure 17:
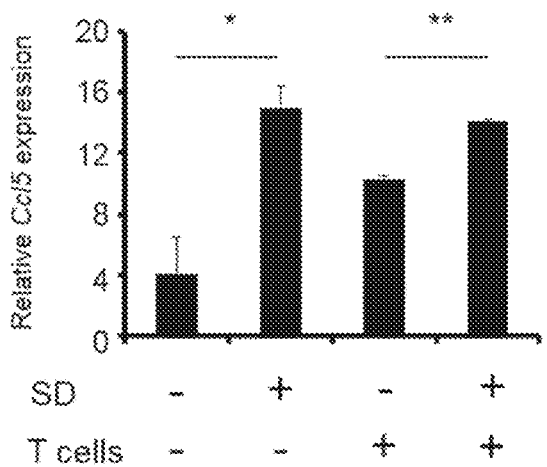
FIG. 17 is a graph showing relative expression levels of CCL5 mRNA at the perivascular tissue of the third ventricular region of each mice groups in Example 1 (1), based on the expression level of HPRT mRNA set to 1.

The relative expression levels of CCL5 in the tissues around the blood vessels in the third ventricular region are shown in FIG. 17. Regardless of transferring EAE-pathogenic CD4 positive T cells, CCL5 expression levels in the mice groups with induction of sleep disorder were increased.

(2) Inflammatory Cytokines

To the mice produced in Example 1 (1) in which sleep disorder was induced followed by transfer of EAE-pathogenic CD4 positive T cells, an anti-IFN-γ antibody, an anti-IL17A antibody, or a control rat IgG antibody (100 μg/mouse each) was intraperitoneally injected daily after transferring EAE-pathogenic CD4 positive T cells, and pathogenic conditions of EAE was evaluated in the same way as in the Example 2 (1). In addition, cell accumulation at the specific blood vessels in the mice 10 days after the transfer of EAE-pathogenic CD4 positive T cells was investigated in the same way as in the Example 2 (4).

Figure 18:
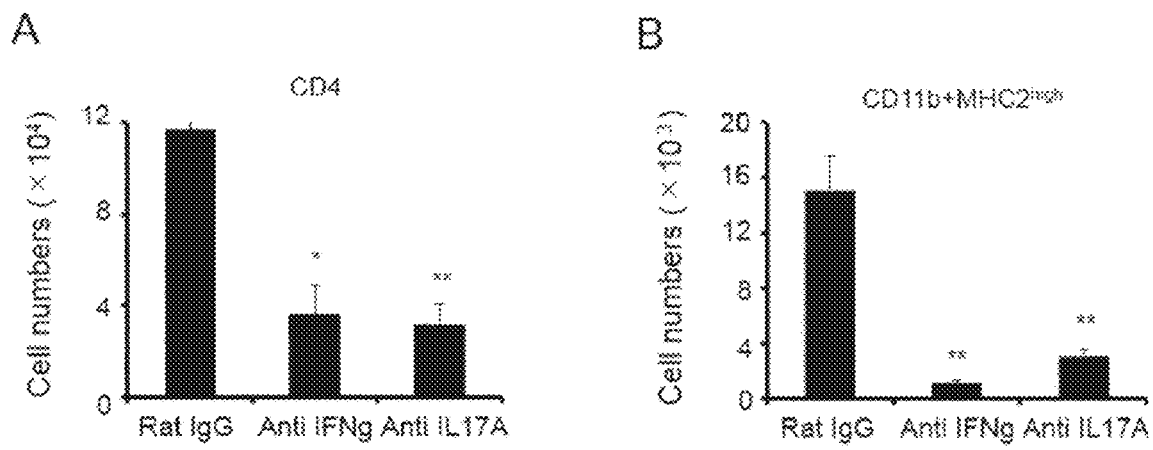
FIG. 18 illustrates a graph showing the numbers of CD4 positive T cells (FIG. 18A) and CD11b positive MHC class II-highly expressing cells (FIG. 18B) in the hippocampi and interbrains of mice in which sleep disorder was induced followed by transfer of EAE-pathogenic CD4 positive T cells, when an anti-IFN-γ antibody, an anti-IL17A antibody, or a rat IgG antibody, control, was administered to the mice.
Figure 19:
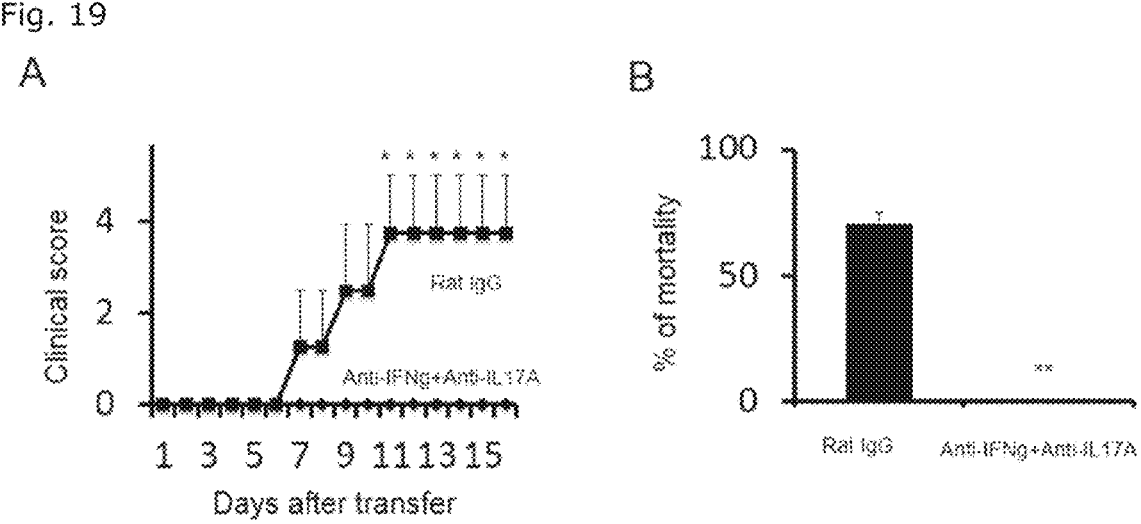
FIG. 19 illustrates graphs indicating pathological conditions of mice in which sleep disorder was induced followed by transfer of EAE-pathogenic CD4 positive T cells, when an anti-IFN-γ antibody+ an anti-IL17A antibody, or a rat IgG antibody, control, was administered to the mice.

Each of the anti-IFN-γ antibody and the anti-IL17A antibody suppressed accumulation of CD4 positive T cells and CDIIb positive MHC class II-highly expressing cells at the specific blood vessels (FIG. 18). Combination use of these antibodies remarkably reduced clinical scores and mortality (FIG. 19).

Then, whether local inflammation in the brain causes a disease was investigated by directly injecting an inflammatory cytokine at the specific blood vessels. The head of a C57BL/6 mouse with induction of sleep disorder or a control mouse was fixed to a stereotactic device under anesthesia, fur above the skull was shaved, and the skin was cleaned with 70% ethanol. A 30-gauge needle was lowered toward the specific blood vessels (coordinates: AP −1.06 mm; ML 1 mm; DV 2.25 mm), and EAE-pathogenic CD4 positive T cells ($1\times10^6$ cells)+bone marrow derived dendritic cells pulsed with MOG ($5\times10^5$ cells), IFN-γ (50 ng; PeproTech, Inc.)+IL-17A (50 ng; R&D Systems, Inc.), or IL-6 (50 ng; Toray Industries, Inc.)+IL-17A (50 ng) in 0.2 μL each were microinjected over 90 seconds as described previously (Kim et al. (2011), Mol. Brain, 19, 4-6).

Figure 20:
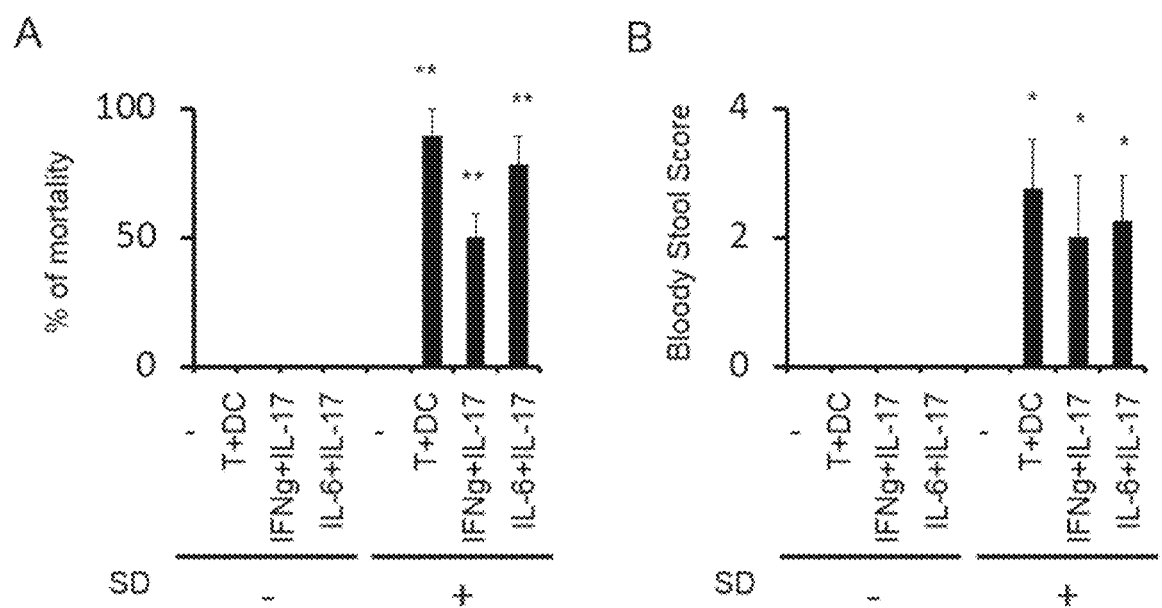
FIG. 20 illustrates graphs indicating pathological conditions of mice in which sleep disorder was induced followed by microinjection of EAE-pathogenic CD4 positive T cells+ bone marrow derived dendritic cells pulsed with myelin oligodendrocyte glycoprotein (MOG) (T+DC), of IFN-γ+ IL-17A, or of IL-6+IL-17A, at specific blood vessels in the boundary area of the third ventricle, thalamus, and dentate gyrus (hereinafter, simply referred to as "specific blood vessel(s)" throughout the present specification).

The mortality of the mice 2 days after microinjection is shown in FIG. 20A, and their bloody stool scores are shown in FIG. 20B. In the mice with induction of sleep disorder, administration of EAE-pathogenic CD4 positive T cells+dendritic cells, IFN-γ+IL-17A, or IL-6+IL-17A caused onset of gastroenteritis, and highly increased mortality.

Thus, it was suggested that, under stress condition, CCL5 produced in the specific blood vessels in the boundary area of the third ventricle, thalamus, and dentate gyrus causes accumulation of EAE-pathogenic CD4 positive T cells to produce inflammatory cytokines, thereby establishes local inflammation in the brain. It was also confirmed that an anti-CCL5 antibody and anti-inflammatory cytokine antibodies improve pathogenic conditions of EAE and gastroenteritis, and reduce mortality.

Example 4 Analysis of the Neural Pathway Involved with Induction of Pathological Conditions in Disease Modeling Mice (1) Connection Between Sympathetic Nerves in the PVN and the Specific Blood Vessels 0.2 μL each of 6-hydroxydopamine (6-OHDA) hydrochloride (2 mg/ml), which is a neurotoxin denaturalizing dopamine/noradrenergic neurons, or a vehicle 0.02% ascorbic acid was microinjected at the specific blood vessels of C57BL/6 mice 4 days before transferring EAE-pathogenic CD4 positive T cells (2 days before stress load), in the same way as in the Example 3 (2). Subsequently, induction of sleep disorder and transfer of EAE-pathogenic CD4 positive T cells were performed in the same way as in the Example 1 (1).

Figure 21:
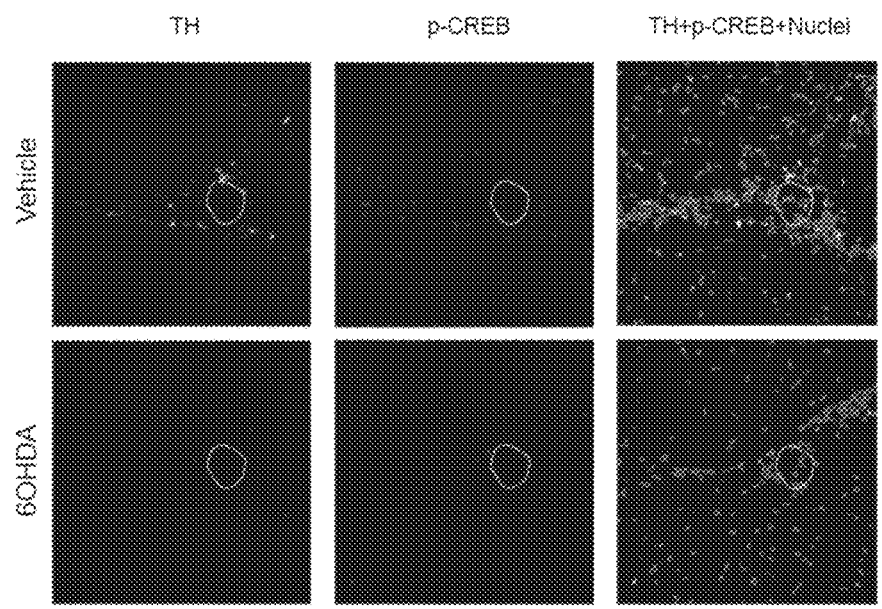
FIG. 21 illustrates photographs of the immunostained third ventricular regions of chemically sympathectomized mice in which sleep disorder was induced followed by transfer of EAE-pathogenic CD4 positive T cells. The immunostaining was performed with an anti-tyrosine hydroxylase antibody (TH) or anti-phosphorylated CREB antibody. The specific blood vessels are within the framework of white dot line.

Photographs of the immunostained third ventricular regions of chemically sympathectomized mice 10 days after transferring EAE-pathogenic CD4 positive T cells are shown in FIG. 21. The immunostaining was performed with an anti-tyrosine hydroxylase antibody or anti-phosphorylated CREB antibody. 6-OHDA reduced tyrosine hydroxylase-positive sympathetic neurons, and suppressed phosphorylation of CREB induced by noradrenergic receptor-mediated signal transduction.

Figure 22:
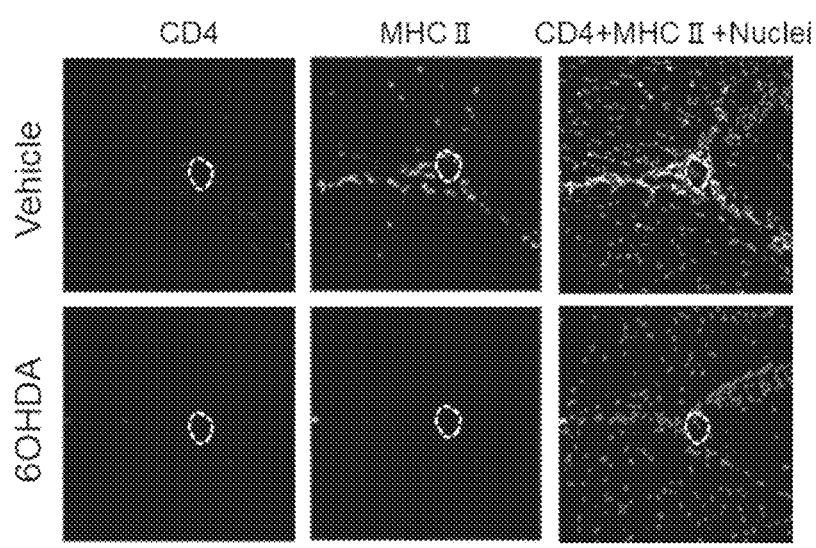
FIG. 22 illustrates photographs of the immunostained third ventricular regions of chemically sympathectomized mice in which sleep disorder was induced followed by transfer of EAE-pathogenic CD4 positive T cells, wherein the immunostaining was performed with an anti-CD4 antibody or anti-MHC class II antibody (FIG. 22A); and graphs showing the numbers of the stained cells (FIG. 22B). The specific blood vessels are within the framework of white dot line in FIG. 22A.
Figure 22:
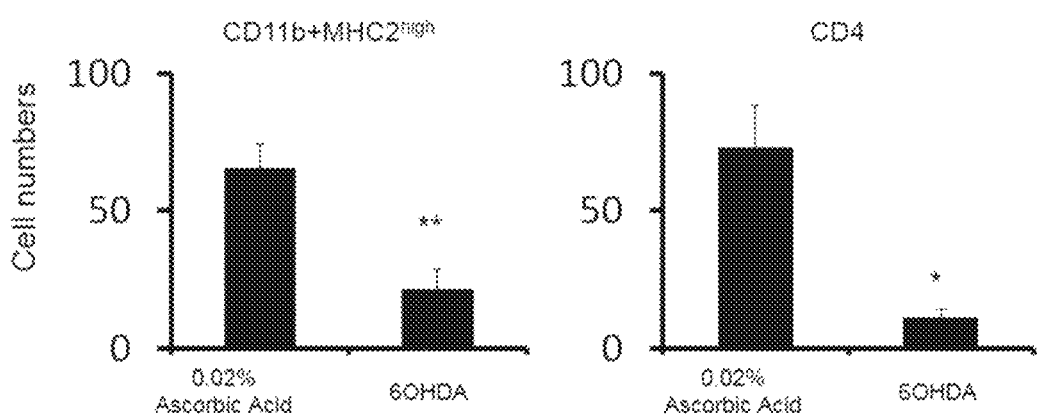
Figure 23:
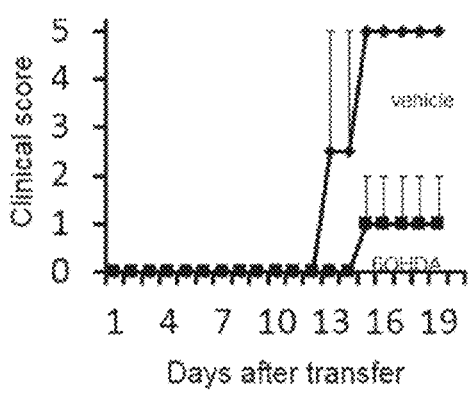
FIG. 23 illustrates graphs indicating pathological conditions of chemically sympathectomized mice in which sleep disorder was induced followed by transfer of EAE-pathogenic CD4 positive T cells.
Figure 23:
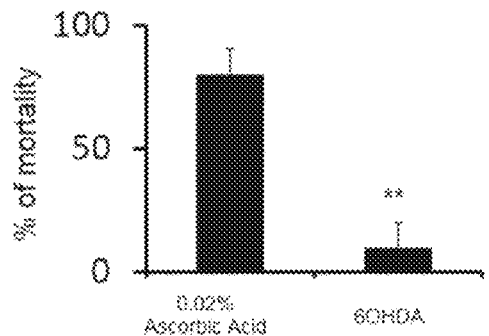

Photographs of the third ventricular regions immunostained with an anti-MHC class II antibody and anti-CD4 antibody, and graphs of the stained cell numbers, are shown in FIG. 22. The clinical scores and mortality of the mice are shown in FIG. 23. Accumulation of CD11b positive MHC class II-highly expressing cells and CD4 positive T cells at the specific blood vessels was suppressed by administration of 6-OHDA, and both of the clinical scores and mortality were improved.

Figure 24:
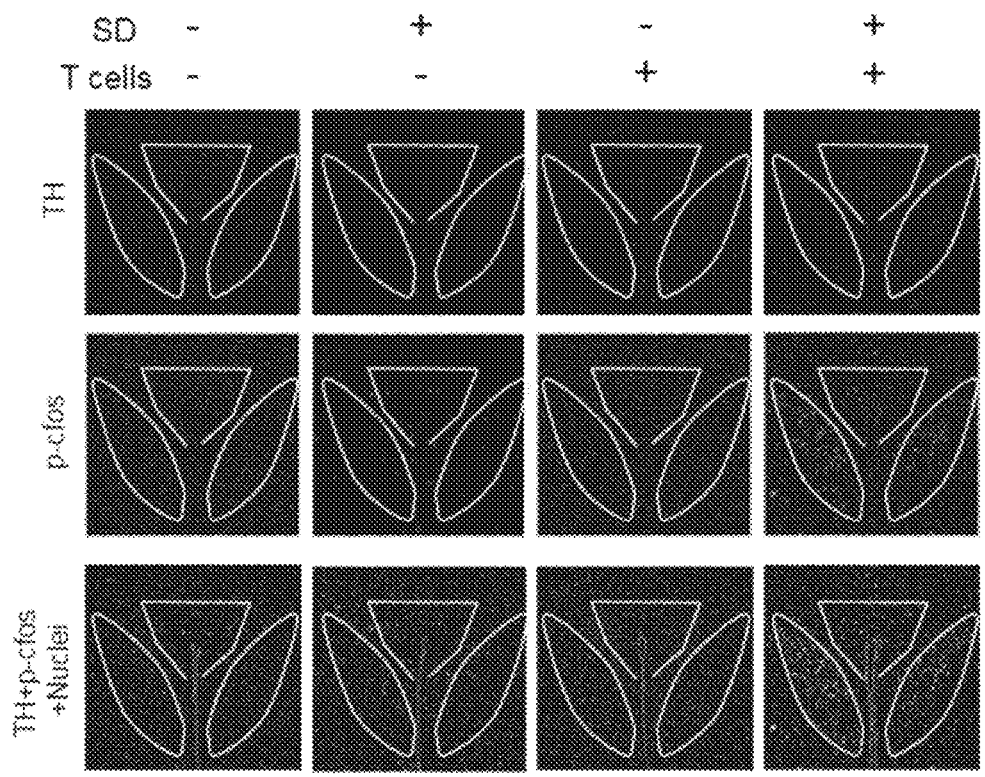
FIG. 24 illustrates photographs of the immunostained hypothalami of each mice groups in Example 1 (1), with an anti-tyrosine hydroxylase antibody (TH) or anti-phosphorylated cfos antibody (FIG. 24A); and graphs showing the numbers of the stained cells (FIG. 24B). In each photograph of FIG. 24A, the paraventricular nucleus (PVN) is within the upper center framework of white dot line, and the dorsal medial hypothalamic nuclei (DMH) are within a matched pair of frameworks of white dot line.
Figure 24:
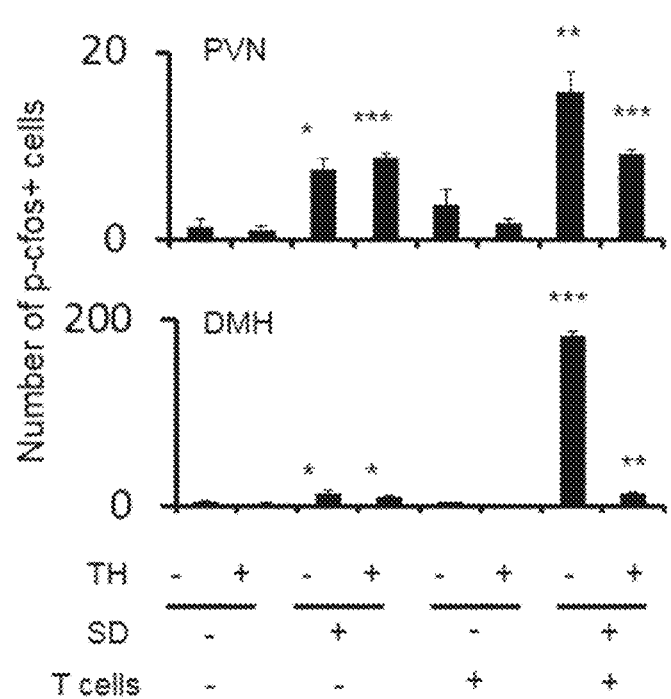

Then, by using each mice produced in Example 1 (1), neural activation in the PVN and DMH was investigated. Photographs of brain sections removed from the mice 10 days after transferring EAE-pathogenic CD4 positive T cells and immunostained with an anti-tyrosine hydroxylase antibody and anti-phosphorylated cfos antibody, and graphs of the stained cell numbers, are shown in FIG. 24. Induction of sleep disorder activated sympathetic neurons in the PVN, and the activation level was enhanced by transferring EAE-pathogenic CD4 positive T cells. When EAE-pathogenic CD4 positive T cells were transferred after induction of sleep disorder, the activation of tyrosine hydroxylase-negative neurons in the DMH was observed.

Figure 25:
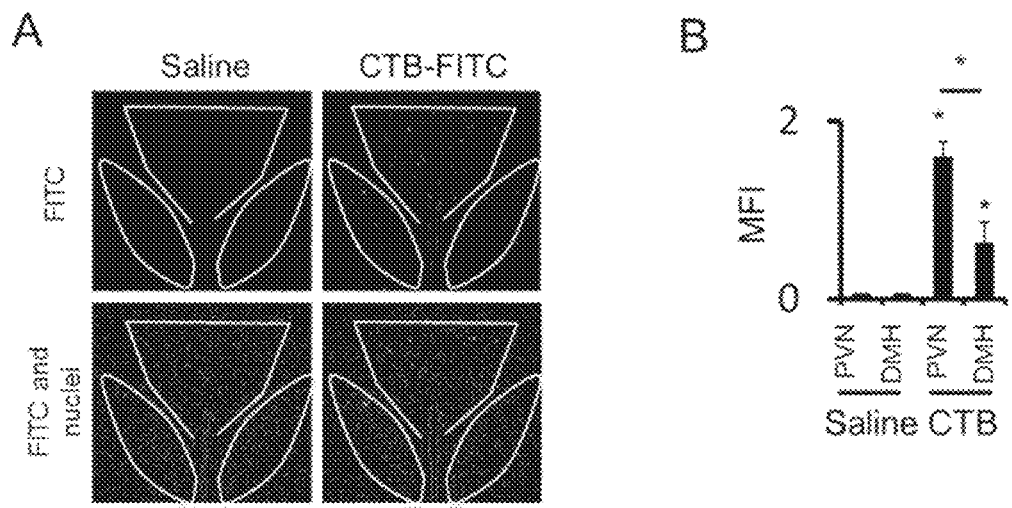
FIG. 25 illustrates fluorescent imaging photographs of the hypothalami of mice in which sleep disorder was induced followed by transfer of EAE-pathogenic CD4 positive T cells (FIG. 25A); and a graph showing the numbers of the fluorescent cells (FIG. 25B), when FITC-conjugated cholera toxin B (FITC-CTB) or the vehicle, saline, was microinjected at the specific blood vessels of the mice. In each photograph of FIG. 25A, the PVN is within the upper center framework of white dot line, and the DMHs are within a matched pair of frameworks of white dot line.
Figure 26:
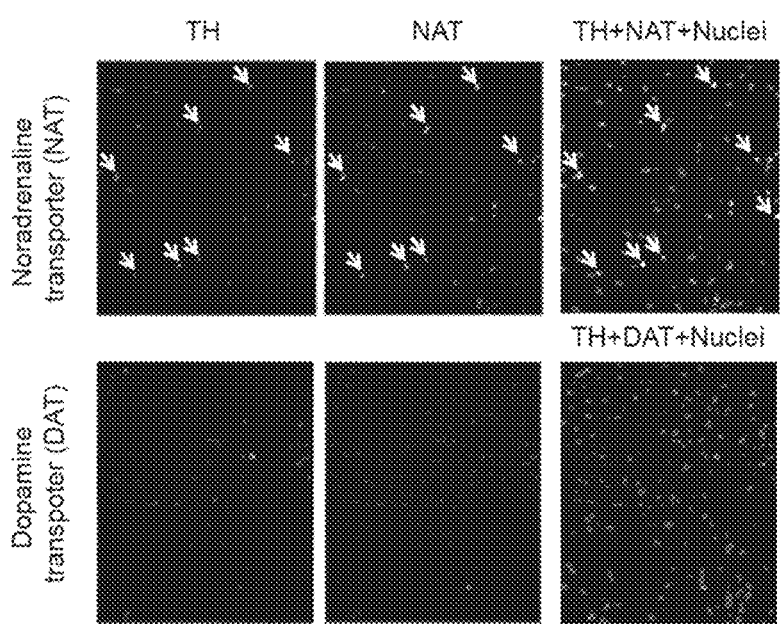
FIG. 26 illustrates photographs of the immunostained PVNs of mice in which sleep disorder was induced followed by transfer of EAE-pathogenic CD4 positive T cells. The immunostaining was performed with an anti-tyrosine hydroxylase antibody (TH), anti-noradrenaline transporter antibody (NAT), and anti-dopamine transporter antibody (DAT).

Furthermore, by using a retrograde tracer, neural connection to the specific blood vessels were investigated. 5 days after transferring EAE-pathogenic CD4 positive T cells, a FITC conjugated cholera toxin B subunit (FITC-CTB) (Sigma-Aldrich Co. LLC., 1 mg/mL), which is a retrograde tracer, or a vehicle saline, was microinjected at the specific blood vessels of mice in which sleep disorder was induced followed by transfer of EAE-pathogenic CD4 positive T cells. Fluorescent photographs of the PVN and DMH, and a graph of the stained cell numbers, are shown in FIG. 25. Fluorescence intensity of FITC-CTB was higher in the PVN than in the DMH. Photographs of the PVN immunostained with an anti-tyrosine hydroxylase antibody, anti-noradrenaline transporter, and anti-dopamine transporter antibody are shown in FIG. 26. Tyrosine hydroxylase-positive neurons at the PVN co-expressed noradrenaline transporter, but did not co-express dopamine transporter.

Thus, it was suggested that the specific blood vessels are directly connected to PVN sympathetic nerves, and under stress condition, these sympathetic neurons secrete noradrenaline and induce chemokines at the specific blood vessels. In addition, it was confirmed that transfer of EAE-pathogenic CD4 positive T cells under stress condition activates DMH nerves. Further tests as following were performed.

(2) Connection Between the Specific Blood Vessels and DMH

Figure 27:
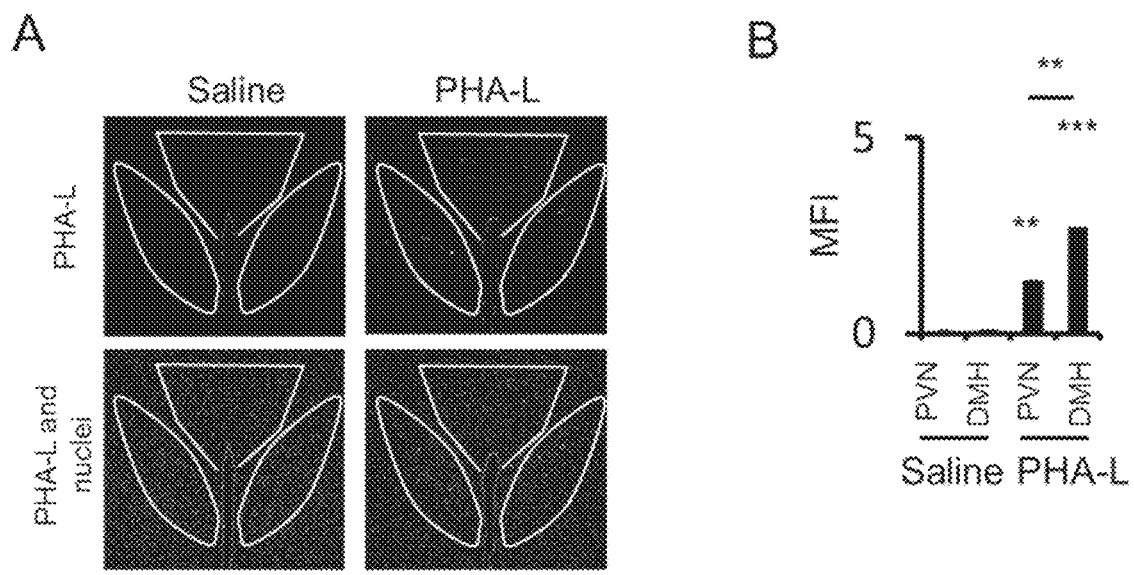
FIG. 27 illustrates fluorescent imaging photographs of the hypothalami of mice in which sleep disorder was induced followed by transfer of EAE-pathogenic CD4 positive T cells (FIG. 27A); and a graph showing the numbers of the fluorescent cells (FIG. 27B), when PHA-L or the vehicle, saline, was microinjected at the specific blood vessels of the mice. In each photograph of FIG. 27A, the PVN is within the upper center framework of white dot line, and the DMHs are within a matched pair of frameworks of white dot line.
Figure 28:
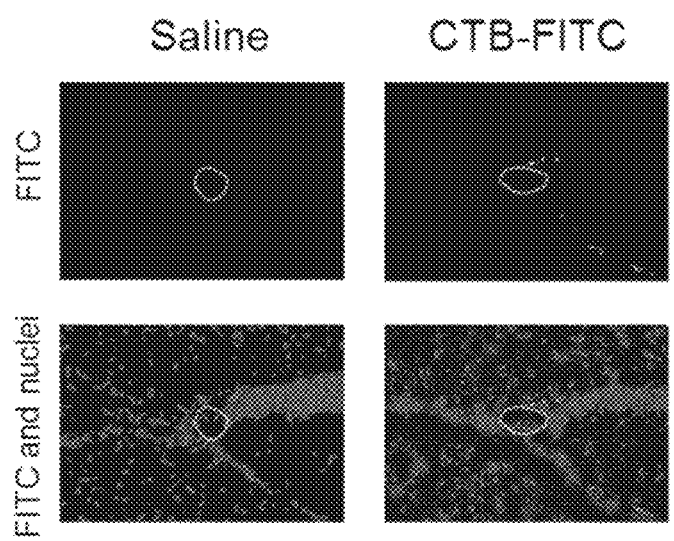
FIG. 28 illustrates fluorescent imaging photographs of the third ventricular regions of mice in which sleep disorder was induced followed by transfer of EAE-pathogenic CD4 positive T cells, when FITC-CTB or the vehicle, saline, was microinjected to the DMH of the mice. The specific blood vessels are within the framework of white dot line.

To the specific blood vessels of the mice produced in Example 1 (1) in which sleep disorder was induced followed by transfer of EAE-pathogenic CD4 positive T cells, an anterograde tracer, PHA-L (25 mg/mL), or a vehicle saline, was microinjected 5 days after the transfer of EAE-pathogenic CD4 positive T cells. Fluorescence intensity of PHA-L was higher in the DMH than in the PVN (FIG. 27). When FITC-CTB was microinjected into DMH (coordinates: AP −1.46 mm; ML 0.37 mm; DV 5 mm), fluorescence of FITC was observed at the specific blood vessels (FIG. 28).

Figure 29:
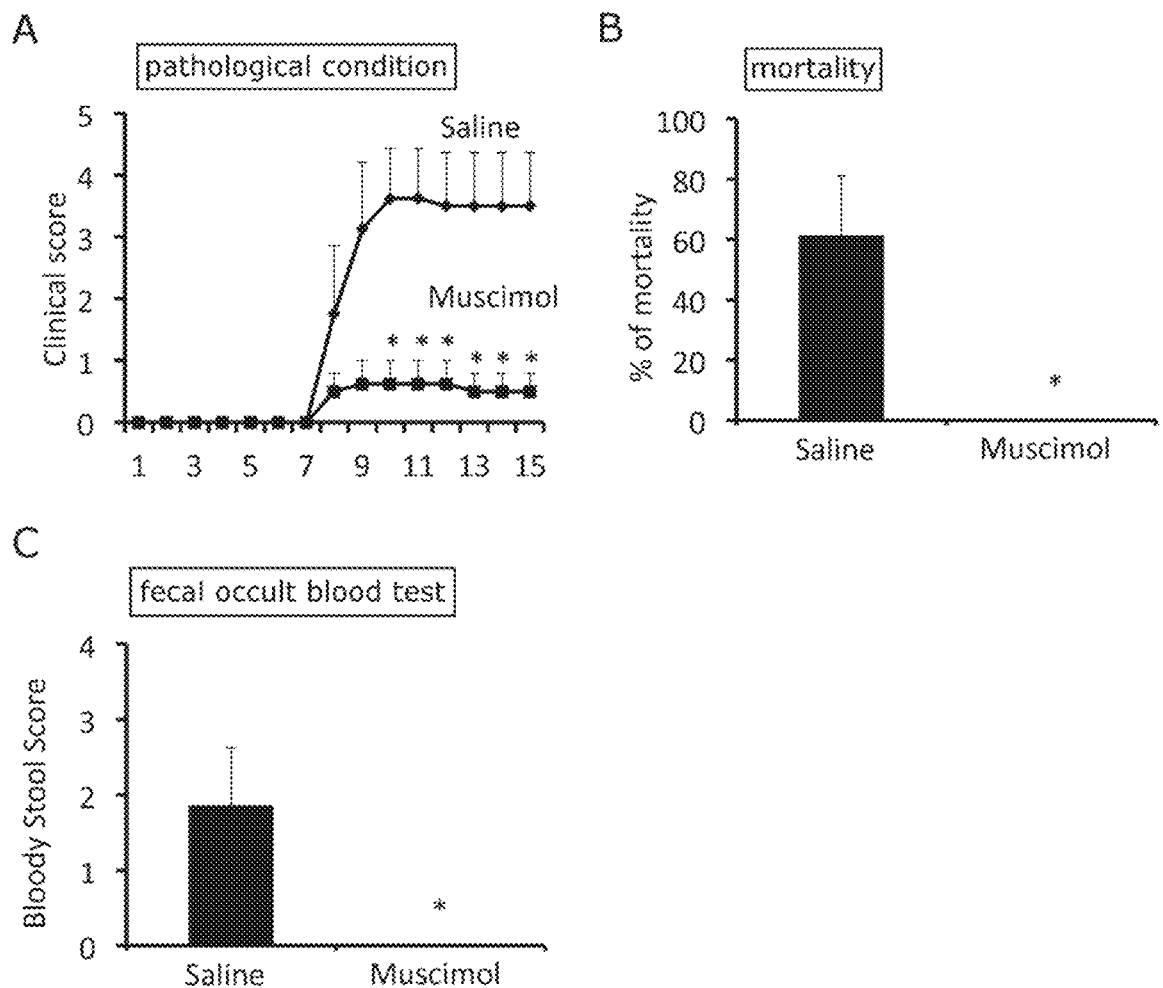
FIG. 29 illustrates graphs indicating pathological conditions of mice in which sleep disorder was induced followed by transfer of EAE-pathogenic CD4 positive T cells, when muscimol was administered to the mice.

In addition, 5 days after transferring EAE-pathogenic CD4 positive T cells, a $GABA_A$ receptor agonist muscimol (Sigma-Aldrich Co. LLC., 0.25 mg/mL), which is known to suppress neural activation, or a vehicle saline was microinjected into the DMH, and clinical scores were evaluated, and 10 days after transferring EAE-pathogenic CD4 positive T cells, mortality and bloody stool scores were evaluated. Muscimol remarkably improved clinical scores, mortality, and bloody stool scores (FIG. 29).

Thus, it was suggested that local inflammation at the specific blood vessels activates DMH neurons, especially tyrosine hydroxylase-negative neurons. In addition, it was confirmed that a GABA receptor agonist improves pathogenic conditions of EAE and gastroenteritis, and reduces mortality.

Figure 30:
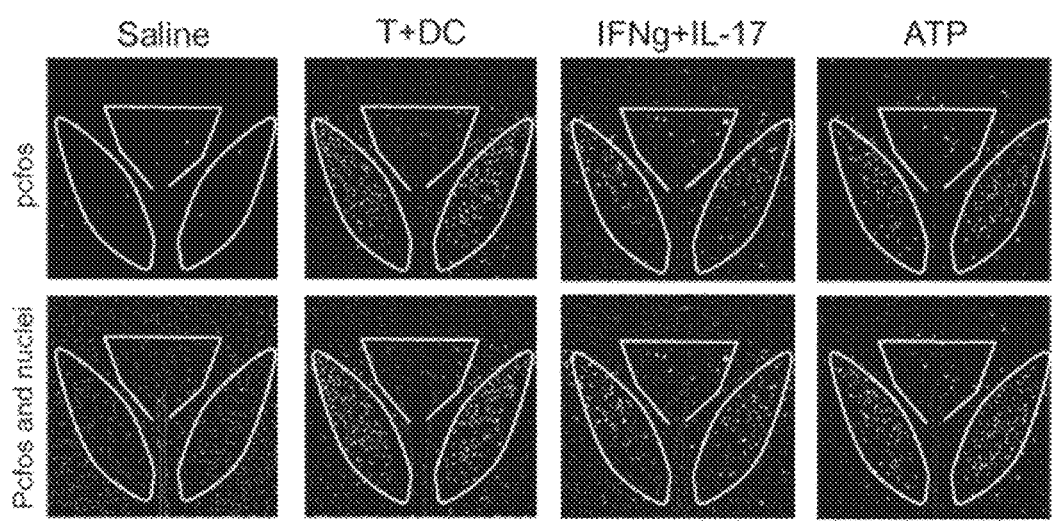
FIG. 30 illustrates photographs of the immunostained hypothalami of mice in which sleep disorder was induced followed by microinjection of EAE-pathogenic CD4 positive T cells+bone marrow derived dendritic cells pulsed with MOG (T+DC), of IFN-γ+IL-17A, or of ATP or of the vehicle, saline, at the specific blood vessels, wherein the immunostaining was performed with an anti-phosphorylated cfos antibody (FIG. 30A); and graphs showing the numbers of the stained cells (FIG. 30B). In each photograph of FIG. 30A, the PVN is within the upper center framework of white dot line, and the DMHs are within a matched pair of frameworks of white dot line.
Figure 30:
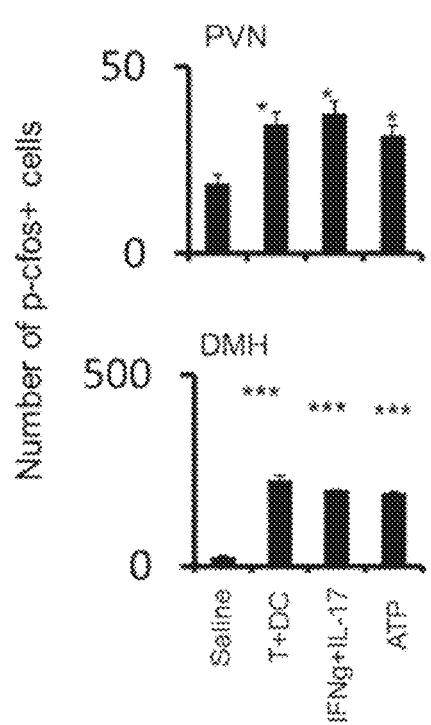

(3) Relationship of Neural Connection Among the PVN, DMH, and Specific Blood Vessels with Pathogenic Conditions At the specific blood vessels of C57BL/6 mice in which sleep disorder was induced, EAE-pathogenic CD4 positive T cells+dendritic cells pulsed with MOG or IFN-γ+IL-17A were microinjected, in the same way as in the Example 3 (2). In the PVN and DMH 2 days after the microinjection, an increase in phosphorylated cfos, that is, neural activation, was observed (FIG. 30).

Figure 31:
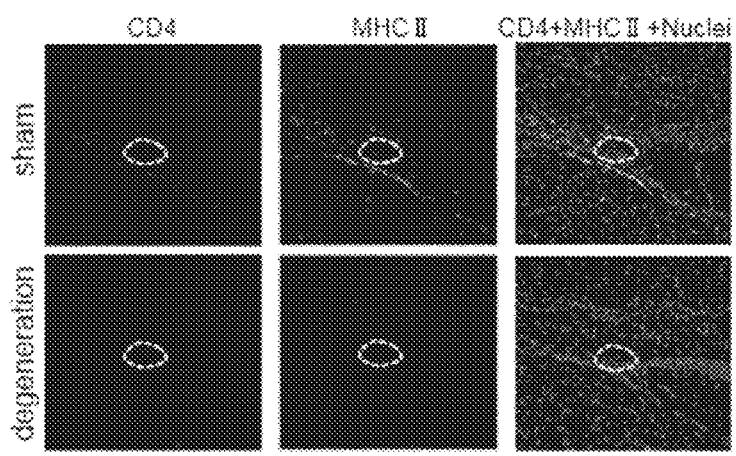
FIG. 31 illustrates photographs of the immunostained third ventricular region of unilaterally PVN-removed mice (degeneration) in which sleep disorder was induced followed by transfer of EAE-pathogenic CD4 positive T cells, wherein the immunostaining was performed with an anti-CD4 antibody or anti-MHC class II antibody (FIG. 31A); and graphs showing the numbers of the stained cells (FIG. 31B).
Figure 31:
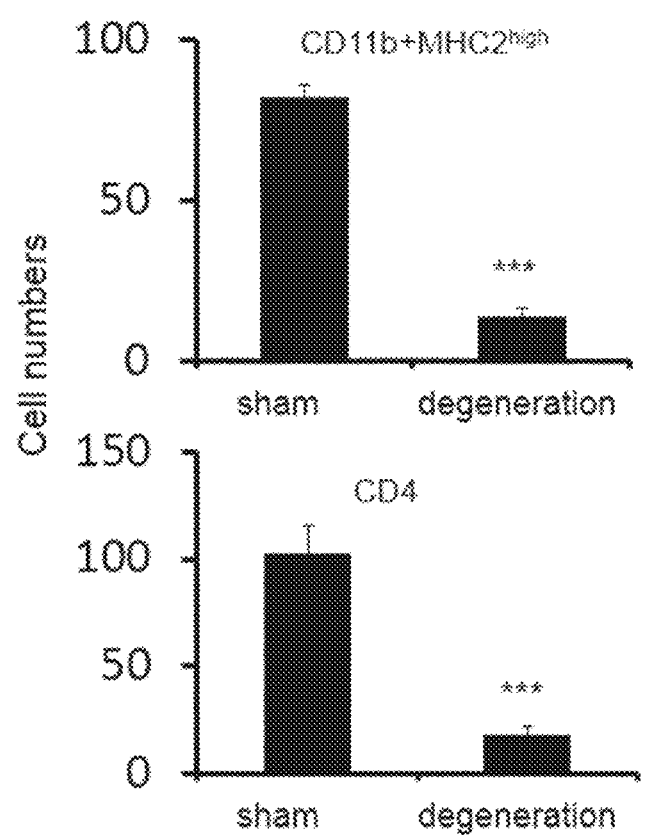
Figure 32:
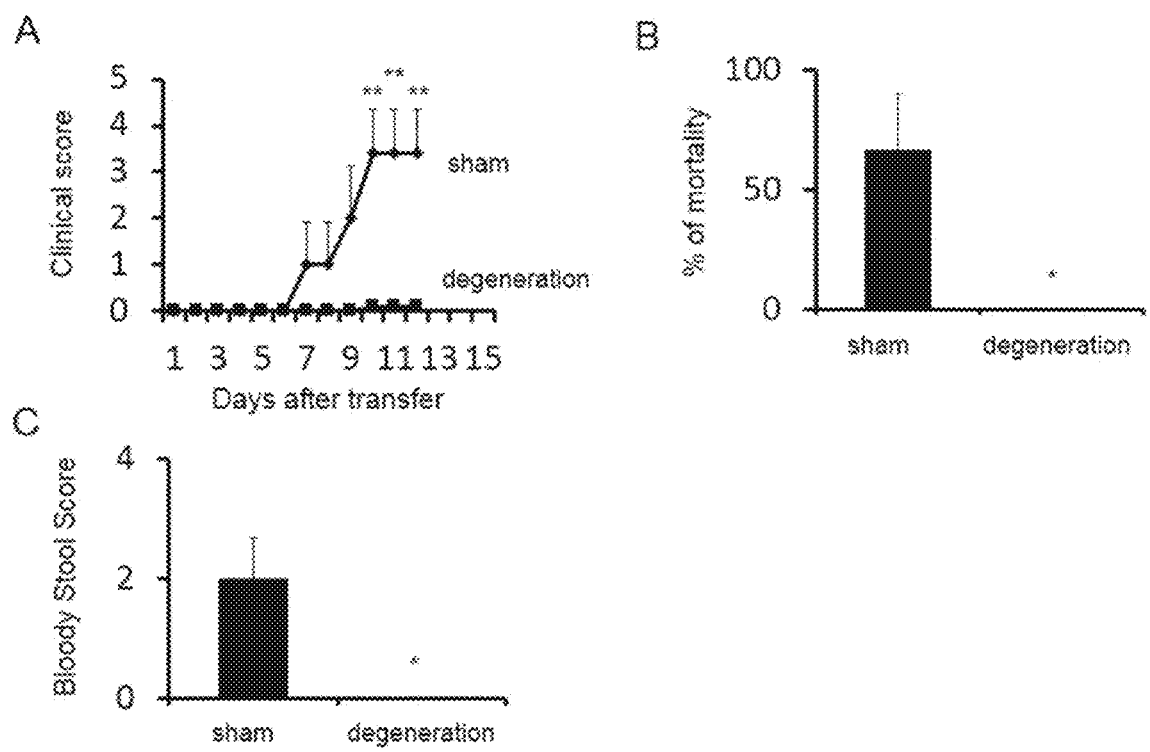
FIG. 32 illustrates graphs indicating pathological conditions of unilaterally PVN-removed mice in which sleep disorder was induced followed by transfer of EAE-pathogenic CD4 positive T cells.

A hole was made in the skull of an anesthetized mouse with a drill, and an electrode (Brain Science Idea, Co., Ltd.) was inserted through the skull hole into the PVN (coordinates: AP −1.06 mm; ML 0.25 mm; DV 4.8 mm). Direct current of 400 µA was loaded for 5 seconds to remove the PVN unilaterally a week before stress load. To the mice, in the same way as in the Example 1 (1), induction of sleep disorder and transfer of EAE-pathogenic CD4 positive T cells were performed. Unilateral remove of PVN suppressed accumulation of CD11b positive MHC class II-highly expressing cells and CD4 positive T cells at the specific blood vessels (FIG. 31), improved pathogenic conditions of EAE and gastroenteritis, and reduced mortality (FIG. 32).

Thus, it was suggested that local inflammation in the brain activates PVN and DMH nerves, and triggers various diseases in the disease modeling mice.

Figure 33:
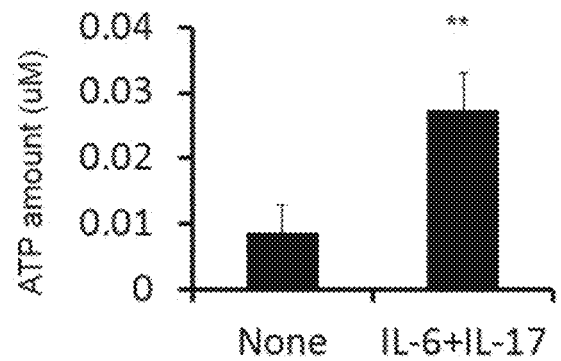
FIG. 33 is a graph showing ATP production amounts of BC1 cells cultured under the presence of IL-6 and IL-17A.

Then, functions of a neurotransmitter, ATP, in neural connection among the PVN, DMH, and specific blood vessels, and its contribution to pathogenic conditions in disease modeling mice, were investigated. Vascular endothelial cell line BC1 cells (given by Professor Masayuki Miyasaka at Osaka University) were cultured in DMEM for 24 hours, then, human IL-6 (50 ng/mL), human soluble IL-6 receptor a (50 ng/mL), and mouse IL-17A (50 ng/mL) were added and further cultured for 24 hours. Intracellular production of ATP was measured with ATP assay kit (TOYO Ink Co., Ltd.). The results are shown in FIG. 33. Stimulation with inflammatory cytokines IL-17A+IL-6 increased ATP production in the vascular endothelial cells.

In addition, PVN and DMH neurons were activated by microinjection of ATP (Sigma-Aldrich, Co. LLD, 2 µg) at the specific blood vessels of mice in which sleep disorder was induced (FIG. 30).

Figure 34:
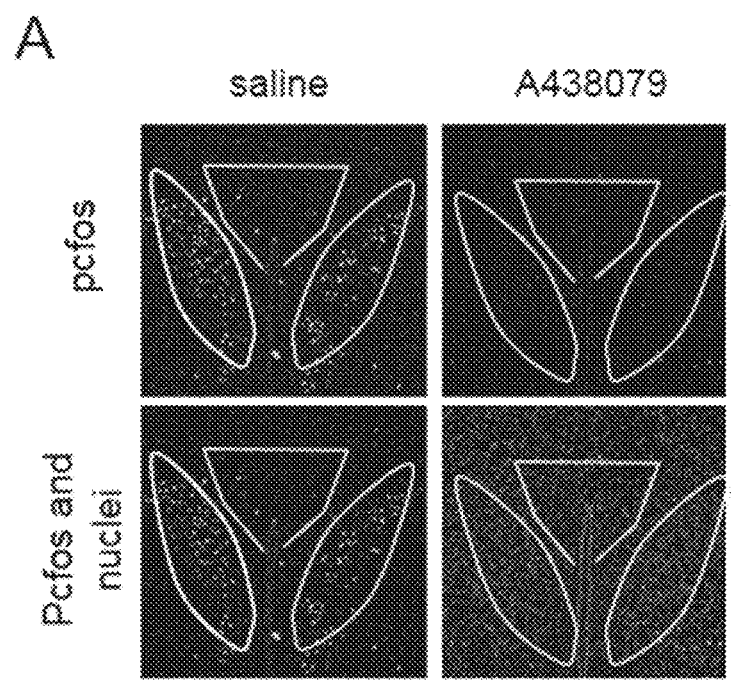
FIG. 34 illustrates photographs of the immunostained hypothalami of mice in which sleep disorder was induced followed by microinjection of A438079 or the vehicle, saline, together with IL-6 and IL-17A, at the specific blood vessels, wherein the immunostaining was performed with an anti-phosphorylated cfos antibody on 2 days after the microinjection (FIG. 34A); and graphs (FIG. 34B) showing the numbers of the stained cells. In each photograph of FIG. 34A, the PVN is within the upper center framework of white dot line, and the DMHs are within a matched pair of frameworks of white dot line.
Figure 34:
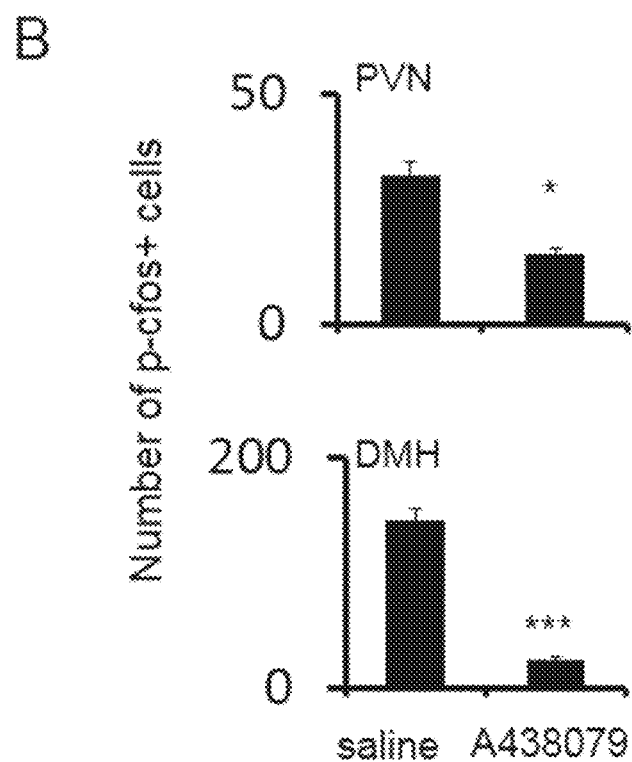
Figure 35:
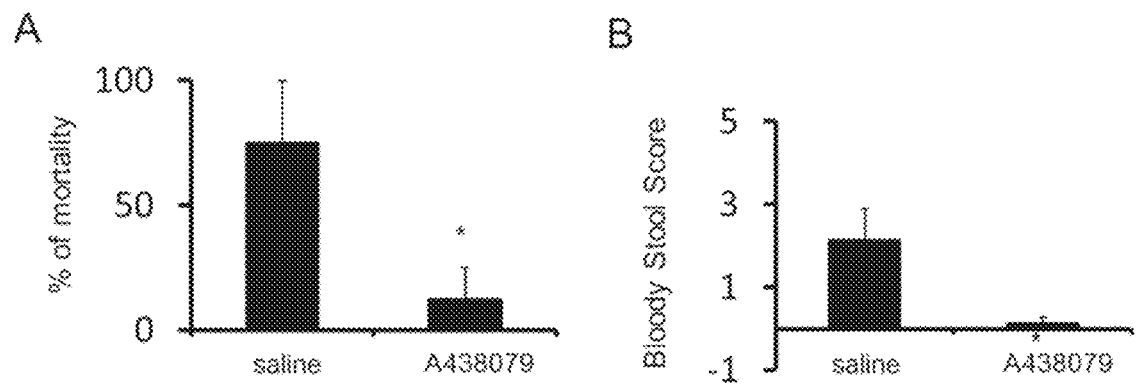
FIG. 35 illustrates graphs indicating pathological conditions of mice in which sleep disorder was induced followed by microinjection of A438079 or the vehicle, saline, together with IL-6 and IL-17A, at the specific blood vessels.

Furthermore, at the specific blood vessels of mice in which sleep disorder was induced, IL-6 and IL-17A, with or without a selective antagonist for P2X receptor which is an ATP receptor, A438079 (1 µg), were microinjected, in the same way as in the Example 3 (2). Phosphorylated cfos in the third ventricular region, bloody stool scores, and mortality were evaluated 2 days after the microinjection, and the results are shown in FIG. 34 and FIG. 35. A438079 suppressed neural activation in the PVN and DMH, and improved gastroenteritis and mortality.

Thus, it was suggested that ATP induced by inflammatory cytokines at local inflammatory position in the brain activates the PVN and DMH, and induces pathological conditions in disease modeling mice. In addition, it was confirmed that the ATP receptor antagonist improves pathogenic conditions of EAE and gastroenteritis, and reduces mortality.

Figure 36:
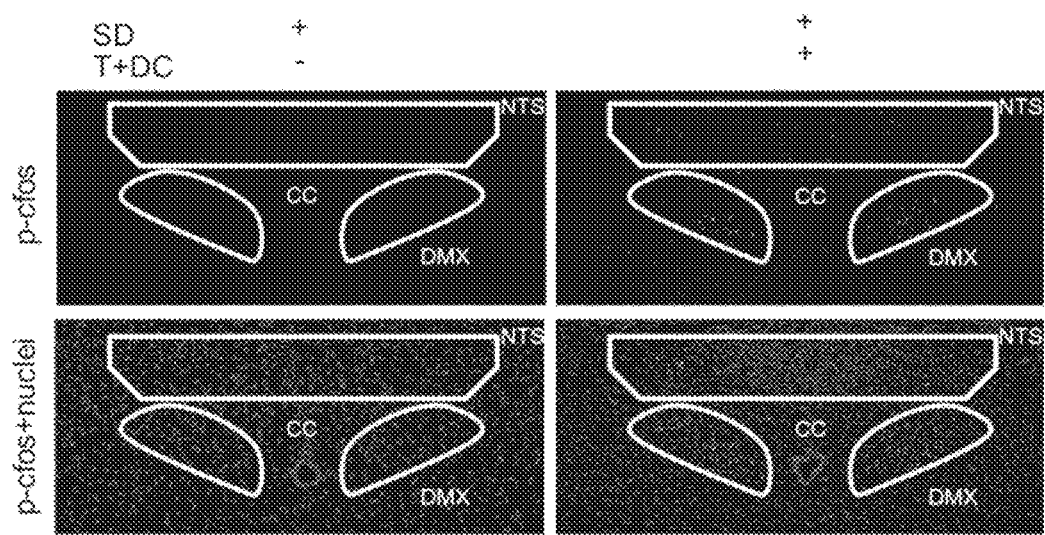
FIG. 36 illustrates photographs showing of the immunostained medullae of mice in which sleep disorder was induced followed by microinjection of EAE-pathogenic CD4 positive T cells+bone marrow derived dendritic cells pulsed with MOG (T+DC), at the specific blood vessels. The immunostaining was performed with an anti-phosphorylated cfos antibody on 2 days after the microinjection. In each photograph, the nucleus tractus solitarii (NTS) is within the upper center framework of white dot line, and the dorsal vagal nuclei (DMXs) are within a matched pair of frameworks of white dot line.

(4) Relationship of the Dorsal Vagal Nucleus (DMX) and Nucleus Tractus Solitarii (NTS) with Pathological Conditions In (2) above, the anterograde tracer PHA-L microinjected at the specific blood vessels reached to the DMX (results not shown). In addition, when EAE-pathogenic CD4 positive T cells+dendritic cells pulsed with MOG were microinjected at the specific blood vessels of mice in which sleep disorder was induced in the same way as in the Example 3 (2), an increase in phosphorylated cfos, that is, neural activation was observed in the DMX, and in the NTS which is a main nucleus of afferent vagal nerves (FIG. 36).

Figure 37:
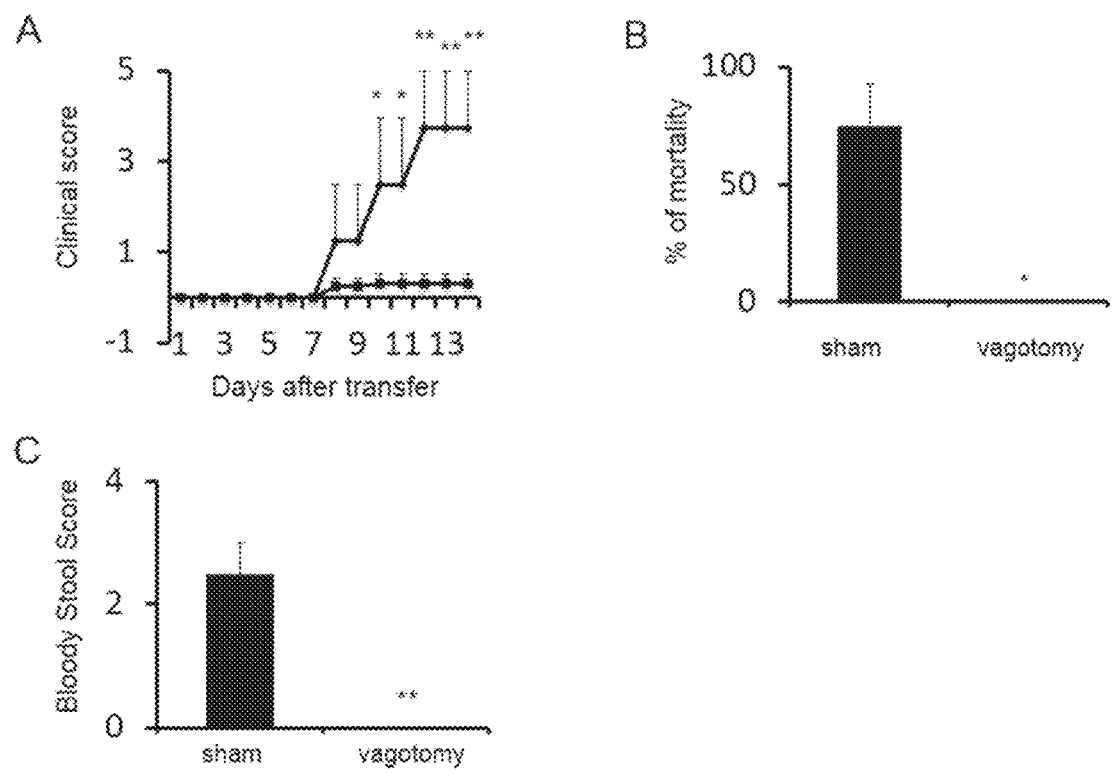
FIG. 37 illustrates graphs indicating pathological conditions of vagotomized mice in which sleep disorder was induced followed by transfer of EAE-pathogenic CD4 positive T cells.

Furthermore, subdiaphragmatic vagotomy was performed to mice as follows. The stomach and lower esophagus of an anesthetized mouse were visualized from an upper midline laparotomy, and the stomach was retracted down beneath the diaphragm to expose both vagal trunks. At least 1 mm of visible vagal nerve was dissected, and all neural and connective tissue surrounding the esophagus immediately below the diaphragm was removed to transect all small vagal branches. To the mice, induction of sleep disorder and transfer of EAE-pathogenic CD4 positive T cells were performed in the same way as in the Example 1 (1) to produce disease modeling mice. Vagotomy improved pathogenic conditions of EAE and gastroenteritis in the disease modeling mice, and reduced mortality (FIG. 37).

Thus, it was suggested that local inflammation in the brain activates the afferent vagal nerves in DMX and NTS, and induces various pathological conditions in the disease modeling mice.

As evident from the results of the Examples 1 to 4, stress load activated PVN sympathetic nerves, made the specific blood vessels in the boundary area of the third ventricle, thalamus, and dentate gyrus, secrete noradrenalin, and caused production of CCL5, accumulation of CD11b positive MHC class II-highly expressing cells and CD4 positive T cells, and production of inflammatory cytokines. Furthermore, a mechanism was estimated that the T cell-accumulating local inflammation in the brain activates DMH nerves via ATP, which in turn triggers various pathological conditions in the disease modeling mice through activating vagus nerves in the DMX and NTS.

Moreover, it was confirmed that suppression, blockade, or inhibition of the neural pathway or CCL5 or inflammatory cytokines involved with the mechanism described above contributes to preventing and/or treating pathological conditions in the disease modeling mice.

Example 5 Analysis of Genes of which Expression at the Specific Cerebral Blood Vessels Change by Stress Load Approximately 100 frozen sections of the brain (a thickness of 15 μm) were prepared from C57BL/6 mice 2 days after induction of sleep disorder, fixed with PAXgene (QIAGEN Inc.) for 15 minutes, then with 100% EtOH for 10 minutes. Tissues around the blood vessels in the third ventricular region in the section were collected with a laser microdissection device, DM6000B (Leica Microsystems Inc.), and total RNA was extracted with RNeasy micro kit (QIAGEN Inc.). RNA sequencing was conducted by Kazusa DNA Res. Inst., and expression analysis of all genes was performed.

Figure 38:
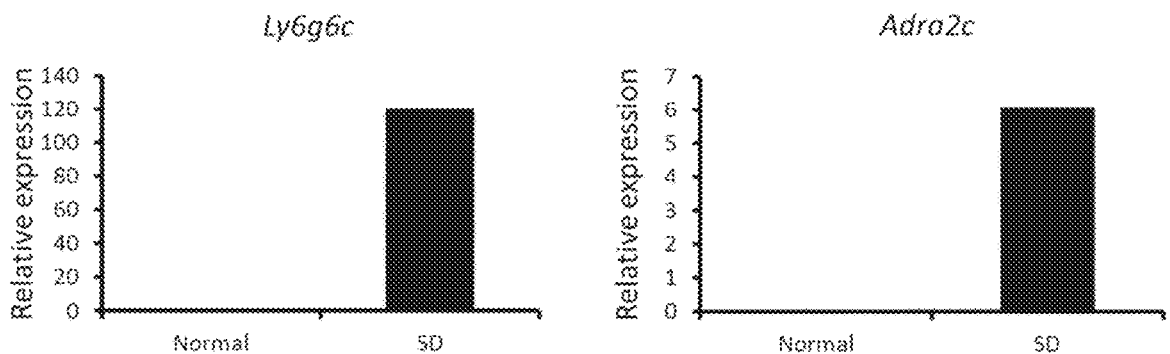
FIG. 38 illustrates graphs showing expression levels of LY6G6C gene and α2C adrenergic receptor gene at the specific blood vessels of mice in which sleep disorder was induced.

As the analysis result, it was confirmed that stress load increases the expression of LY6G6C gene and α2C adrenalin receptor gene (FIG. 38). The possibility that these factors are involved with inflammation at the specific cerebral blood vessels and pathological conditions in the disease modeling mice was indicated.

Example 6 Improvement of Pathological Conditions in Disease Modeling Mice by Anti-LY6G6C Antibody and Anti-α2C Adrenergic Receptor Antibody Sleep disorder was induced in C57BL/6 mice, and EAE pathologic CD4 positive T cells were transferred into the mice. 5 days after, the head of the mouse was fixed to a stereotactic device under anesthesia, fur above the skull was shaved, and the skin was cleaned with 70% ethanol. A 30-gauge needle was lowered toward the specific blood vessels (coordinates: AP −1.06 mm; ML 1 mm; DV 2.25 mm), and 0.5 μl of an anti-LY6G6C antibody (clone; NIMP-R14) 0.1 mg/mL (NOVUS BIOLOGICALS, LLC), anti-alpha 2C Adrenergic Receptor antibody 1 mg/mL (GeneTex, Inc.), or each control antibodies (rat IgG (Sigma-Aldrich, Co. LLD) or rabbit IgG (Sigma-Aldrich, Co. LLD)) were microinjected over 90 seconds. Subsequently, pathological conditions of the mice were observed over time.

Figure 39:
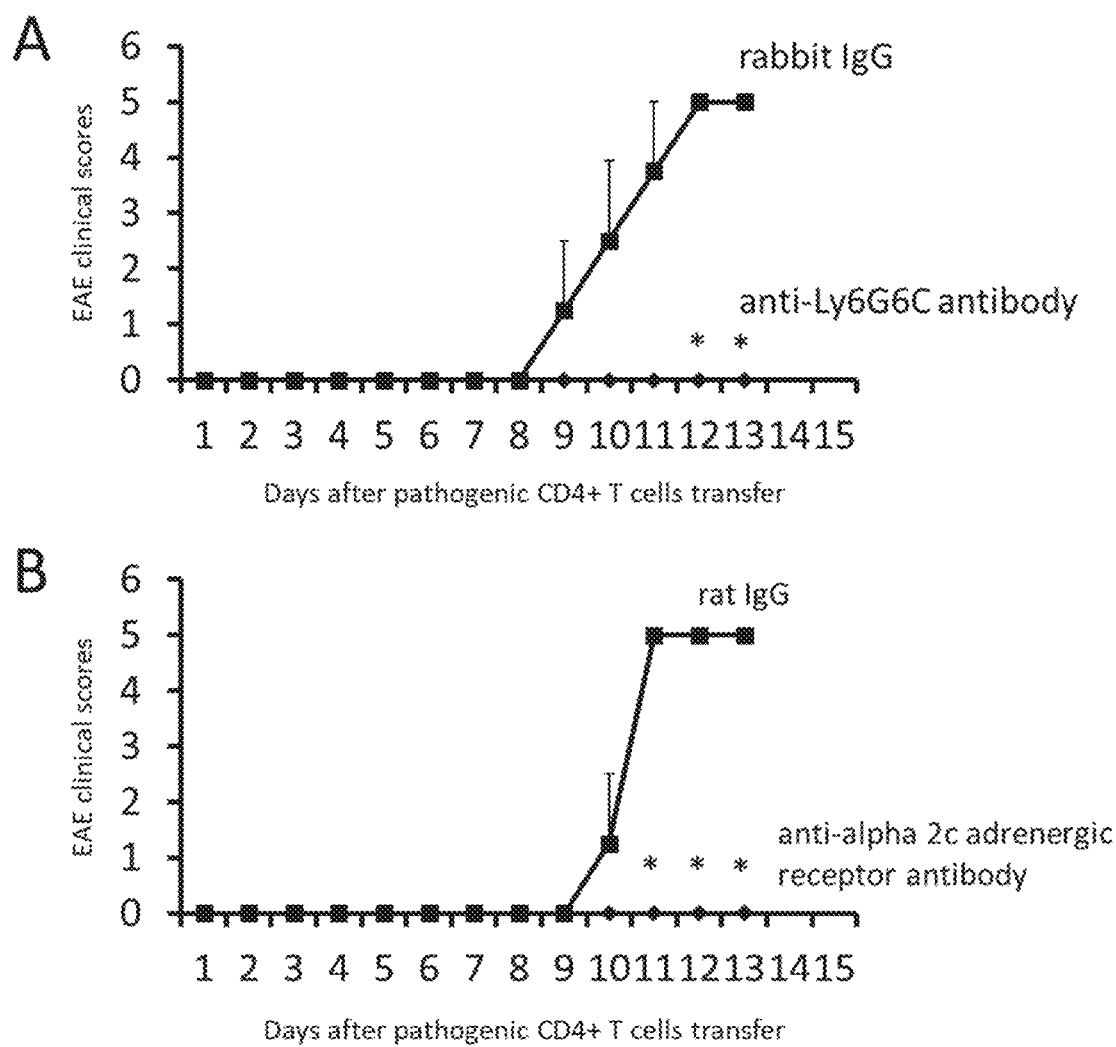
FIG. 39 illustrates graphs indicating pathological conditions of mice in which sleep disorder was induced followed by transfer of EAE-pathogenic CD4 positive T cells, and by microinjection of an anti-LY6G6C antibody or anti-α2C adrenergic receptor antibody.

Changes over time of EAE clinical scores of mice to which the anti-LY6G6C antibody was administered are shown in FIG. 39A, and changes over time of EAE clinical scores of mice to which the anti-α2C adrenergic receptor antibody was administered are shown in FIG. 39B. A rapid increase in clinical scores was observed in the control groups, while no increase in clinical scores was observed and the progression of pathological conditions was significantly suppressed in the anti-LY6G6C antibody-treated group and anti-α2C adrenergic receptor antibody-treated group. Thus, it was confirmed that suppression, blockade, or inhibition of LY6G6C or α2C adrenergic receptor contributes to preventing and/or treating pathological conditions in the disease modeling mice.

Sequence Listing Free Text
SEQ ID NO: 1 Mouse HPRT forward primer
SEQ ID NO: 2 Mouse HPRT reverse primer
SEQ ID NO: 3 Mouse HPRT probe
SEQ ID NO: 4 Mouse CCL5 forward primer
SEQ ID NO: 5 Mouse CCL5 reverse primer
SEQ ID NO: 6 Mouse CCL5 probe

The invention claimed is:

1. A method for producing a mouse model of a disease having inflammation at a cerebral blood vessel, comprising intravenous administration of CD4-positive T-cells reactive to myelin oligodendrocyte glycoprotein (MOG) to a test mouse under chronic mental stress, leading to inflammation at a cerebral blood vessel in the brain of the test mouse,
   wherein the chronic mental stress is selected from the group consisting of sleep deprivation, perpetual avoidance from water on a wheel (PAWW) stress, wet bedding, social defeat stress, and maternal separation stress.

2. The method according to claim 1, wherein the cerebral blood vessel is a blood vessel in the boundary area of the third ventricle, thalamus, and dentate gyrus.

3. The method according to claim 1, wherein the disease is selected from the group consisting of progressive multiple sclerosis, gastroenteritis, myocardial disorder, and sudden death.

4. The method according to claim 1, further comprising:
   (i) administering a test substance to the test mouse under the chronic mental stress, and
   (ii) observing development, progression, or occurrence of a disease selected from the group consisting of cerebrovascular inflammation, progressive multiple sclerosis, gastroenteritis, myocardial disorder, and sudden death, in the test mouse.

5. The method of claim 4, wherein the test substance is administered to the test mouse under the chronic mental stress before the start of the intravenous administration of the CD4-positive T-cells reactive to the MOG to the test mouse under the chronic mental stress, further comprising comparing the development, progression, or occurrence of the disease in the test mouse under the chronic mental stress with that in a control mouse under the chronic mental stress to which control mouse the CD4-positive T cells reactive to the MOG are intravenously administered and the test substance is not administered, wherein a reduction in or inhibition of the development, progression, or occurrence of the disease in the test mouse under the chronic mental stress as compared with that in the control mouse under the chronic mental stress indicates that the test substance is effective for preventing the disease.

6. The method of claim 4, wherein the test substance is administered to the test mouse after the start of the intravenous administration of the CD4-positive T cells reactive to the MOG to the test mouse, further comprising comparing the development, progression, or occurrence of the disease in the test mouse with that in a control mouse under the chronic mental stress to which control mouse the CD4-positive T cells reactive to the MOG are intravenously administered and the test substance is not administered, wherein a reduction in or inhibition of the development, progression, or occurrence of the disease in the test mouse under the chronic mental stress as compared with that in the control mouse under the chronic mental stress indicates that the test substance is effective for treating the disease.

7. The method of claim 1, wherein the chronic mental stress is selected from the group consisting of perpetual avoidance from water on a wheel (PAWW) stress, wet bedding, social defeat stress, and maternal separation stress.

8. The method of claim 7, wherein the chronic mental stress is PAWW stress and the test mouse suffers from sleep disorder.

9. The method of claim 1, wherein expression of a molecule is enhanced at a perivascular tissue in the boundary area of the third ventricle, thalamus, and dentate gyrus in the test mouse under the chronic mental stress as compared with that in a control mouse not under the chronic mental stress, wherein the molecule is selected from the group consisting of CC chemokine ligand 5 (CCL5), lymphocyte antigen 6 family member G6C (LY6G6C) and α2C adrenergic receptor.

10. The method of claim 9, wherein the molecule is CCL5.

11. The method of claim 9, wherein the molecule is LY6G6C.

12. The method of claim 9, wherein the molecule is α2C adrenergic receptor.

13. The method of claim 1, wherein the chronic mental stress is sleep deprivation.

14. The method of claim 1, wherein the chronic mental stress is wet bedding.

* * * * *

```
SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: mouse HPRT forward primer

<400> SEQUENCE: 1
agccccaaaa tggttaaggt tg                                              22

<210> SEQ ID NO 2
<211> LENGTH: 23
<212> TYPE: DNA
<213> ORGANISM: Artificial Sequence
<220> FEATURE:
<223> OTHER INFORMATION: mouse HPRT reverse primer

<400> SEQUENCE: 2
caagggcata tccaacaaca aac                                             23

<210> SEQ ID NO 3
<211> LENGTH: 30
<212> TYPE: DNA
<213> ORGANISM: Artificial Sequence
<220> FEATURE:
<223> OTHER INFORMATION: mouse HPRT probe

<400> SEQUENCE: 3
atccaacaaa gtctggcctg tatccaacac                                      30
```

```
<210> SEQ ID NO 4
<211> LENGTH: 20
<212> TYPE: DNA
<213> ORGANISM: Artificial Sequence
<220> FEATURE:
<223> OTHER INFORMATION: mouse CCL5 forward primer

<400> SEQUENCE: 4
ctccctgctg ctttgcctac                                          20

<210> SEQ ID NO 5
<211> LENGTH: 22
<212> TYPE: DNA
<213> ORGANISM: Artificial Sequence
<220> FEATURE:
<223> OTHER INFORMATION: mouse CCL5 reverse primer

<400> SEQUENCE: 5
cggttccttc gagtgacaaa ca                                       22

<210> SEQ ID NO 6
<211> LENGTH: 27
<212> TYPE: DNA
<213> ORGANISM: Artificial Sequence
<220> FEATURE:
<223> OTHER INFORMATION: mouse CCL5 probe

<400> SEQUENCE: 6
tgcctcgtgc ccacgtcaag gagtatt                                  27
```